US011122972B2

(12) United States Patent
Cohen et al.

(10) Patent No.: US 11,122,972 B2
(45) Date of Patent: Sep. 21, 2021

(54) DEVICE AND METHOD FOR DETERMINATION OF PUPIL SIZE IN A SUBJECT HAVING CLOSED EYELIDS

(71) Applicants: HADASIT MEDICAL RESEARCH SERVICES AND DEVELOPMENT LTD., Jerusalem (IL); YISSUM RESEARCH DEVELOPMENT COMPANY OF THE HEBREW UNIVERSITY OF JERUSALEM LTD., Jerusalem (IL)

(72) Inventors: Jose Cohen, Jerusalem (IL); Vladimir Goldman, Tzur Hadassa (IL); Yousef Nadim Farraj, Ben Nadim (IL); Amnon Buxboim, Tel Aviv (IL); Yoav Mintz, Jerusalem (IL); Elchanan Fried, Jerusalem (IL); Gahl Levy, Ramat Gan (IL); Tsevi Beatus, Jerusalem (IL); Yoav Kan-Tor, Rehovot (IL)

(73) Assignees: HADASIT MEDICAL RESEARCH SERVICES AND DEVELOPMENT LTD., Jerusalem (IL); YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 322 days.

(21) Appl. No.: 16/304,199

(22) PCT Filed: Jun. 15, 2017

(86) PCT No.: PCT/IL2017/050668
§ 371 (c)(1),
(2) Date: Nov. 23, 2018

(87) PCT Pub. No.: WO2017/216800
PCT Pub. Date: Dec. 21, 2017

(65) Prior Publication Data
US 2019/0282086 A1  Sep. 19, 2019

Related U.S. Application Data

(60) Provisional application No. 62/350,751, filed on Jun. 16, 2016.

(51) Int. Cl.
*A61B 3/11* (2006.01)
*A61B 3/00* (2006.01)
(Continued)

(52) U.S. Cl.
CPC ............ *A61B 3/112* (2013.01); *A61B 3/0008* (2013.01); *A61B 3/0025* (2013.01); *A61B 3/10* (2013.01);
(Continued)

(58) Field of Classification Search
CPC .. A61B 3/112; A61B 3/11; A61B 3/10; A61B 3/0008; A61B 3/0025; A61B 3/14; A61B 8/10; A61B 2090/502
(Continued)

(56) References Cited

U.S. PATENT DOCUMENTS 4,007,980 A * 2/1977 Bracher ................. A61B 3/112
351/219
5,777,719 A * 7/1998 Williams ............... A61B 3/156
351/212
(Continued)

FOREIGN PATENT DOCUMENTS

JP   UM 3137375   10/2007
JP   2007-531579   11/2007
(Continued)

OTHER PUBLICATIONS

Almohimeed, et al, Development of wearable and flexible ultrasonic sensor for skeletal muscle monitoring, Joint UFFC, EFTC and PFM Symposium, 2013, pp. 1137-1140.
(Continued)

*Primary Examiner* — Mohammed A Hasan
(74) *Attorney, Agent, or Firm* — The Roy Gross Law Firm, LLC; Roy Gross

(57) ABSTRACT

Devices and method for determining a pupil size of a subject having closed eyelids.

18 Claims, 10 Drawing Sheets

(51) Int. Cl.
*A61B 3/14* (2006.01)
*A61B 8/10* (2006.01)
*A61B 3/10* (2006.01)
*A61B 90/50* (2016.01)

(52) U.S. Cl.
CPC .................. *A61B 3/11* (2013.01); *A61B 3/14* (2013.01); *A61B 8/10* (2013.01); *A61B 2090/502* (2016.02)

(58) Field of Classification Search
USPC .......................................................... 351/212
See application file for complete search history.

(56) References Cited

U.S. PATENT DOCUMENTS

| | | | |
|---|---|---|---|
| 6,126,607 | A | 10/2000 | Whitmore, III et al. |
| 2011/0077548 | A1 | 3/2011 | Torch |
| 2014/0185010 | A1 | 7/2014 | Bernert et al. |
| 2014/0343432 | A1 | 11/2014 | Humayun |
| 2016/0073874 | A1 | 3/2016 | Tsai et al. |
| 2016/0270656 | A1* | 9/2016 | Samec ............... G02B 27/0093 |

FOREIGN PATENT DOCUMENTS

| | | |
|---|---|---|
| JP | 2008-543352 | 12/2008 |
| JP | 2010-017205 | 1/2010 |
| JP | 011-508651 | 3/2011 |
| JP | 2013-248312 | 12/2013 |
| JP | 2013-248313 | 12/2013 |
| WO | 2007104870 | 9/2007 |

OTHER PUBLICATIONS

Zhou, et al, Pupil ultrasound images segmentation and diameter measurements based on improved graph cuts, Chinese Journal of Biomedical Engineering, 2015, vol. 34, No. 4, pp. 399-406.
SonicEye Dual-Plane Ultrasound Probe, Retrieved on Feb. 21, 2019, <http://sonivate.com/products/soniceye/>.
The next wave in ultrasound technology, Retrieved on Feb. 21, 2019, <http://www.ultrasoundschoolsinfo.com/next-wave-ultrasound-technology/>.
Miniaturizing a wearable ultrasound pain therapy device (2014), Retrieved on Feb. 21, 2019, <http://www.medicaldesignbriefs.com/component/content/article/mdb/features/19673>.
International Search Report PCT/IL2017/050668 completed Sep. 28, 2017; dated Sep. 28, 2017 5 pages.
Written Opinion of the International Searching Authority PCT/IL2017/050668 dated Sep. 28, 2017 5 pages.
Harries et al. (2010) Ultrasound assessment of extraocular movements and pupillary light reflex in ocular trauma, Amn J of Emergency Medicine, vol. 28, No. 8, pp. 956-959.

\* cited by examiner

DEVICE AND METHOD FOR DETERMINATION OF PUPIL SIZE IN A SUBJECT HAVING CLOSED EYELIDS

CROSS REFERENCE TO RELATED APPLICATIONS

This application is a national phase of PCT Patent Application No. PCT/IL2017/050668 filed Jun. 15, 2017, which claims the benefit of priority of U.S. Provisional Patent Application No. 62/350,751, filed Jun. 16, 2016, the contents of which are all incorporated herein by reference in their entirety.

TECHNICAL FIELD

The present disclosure generally relates to the field of pupil size assessment.

BACKGROUND

Frequent pupil evaluation is part of the protocol for care of critically injured or ill patients. The pupillary light reflex (PLR) and pupil size have traditionally been used as a clinical parameter and as a prognostic indicator. The Brain Trauma Foundation and the American Association of Neurological Surgeons recommends that pupillary light reflex for each eye be used as a prognostic parameter and that the duration of pupillary dilation and fixation be documented.

Different neuroanatomical pathways are involved in the control of the pupil, and the integrity and functionality of these neurological pathways can often be ascertained through the analysis and interpretation of pupillary behavior. This makes the pupil size and the pupillary light reflex an important factor to be considered in many clinical conditions:

- In the management and prognosis of severe traumatic brain injury (TBI), abnormalities in pupillary responses and/or anisocoria (pupil size asymmetry) are often associated with neurological deteriorations, and correlated with poor neurological outcome.
- Blood flow imaging performed on neurological intensive care unit (ICU) patients has shown that pupillary changes are highly correlated with brainstem oxygenation and perfusion/ischemia.
- The decision to triage patients into either conservative therapy or surgical evacuation of mass lesions is typically based on the status of the pupils.
- Pupillary examination is a major tool for clinical evaluation of comatose patients. Unilaterally or bilaterally fixed and dilated pupils (FDPs) are indicative of an emergency and correlated with poor prognosis. Thus, immediate decision making on diagnostic and therapeutic procedures is typically based on pupil evaluation.

Currently, most pupil measurements are conducted by visual observation performed by nursing staff. The patients' eyelids are lifted open and pupillary size and light reactivity (also referred to herein as pupillary reflex) are estimated by visual observation or at best by measuring using a ruler, and pupils' reactivity is assessed using a penlight. Typically, a change greater than 1 mm in pupillary diameter is considered pathologically significant.

However, such manual pupillary assessment is subject to inaccuracies and inconsistencies, and is characterized by large inter-examiner variability. Moreover, ambient light conditions can affect the validity of the visual assessment of the pupil and increase the inter-observer disagreement. These factors may include, for example, poor lighting conditions in the patient's room, the examiner's visual acuity, as well as his/hers distance and orientation with respect to the patient's eye.

Moreover, the manual evaluation requires the nurse to attend to the patient, thus making it a time consuming, labor-intensive assessment, which most often is only performed at routine visits hours apart. As a result, a change in pupil size is seldom detected as it occurs, despite the fact that immediate medical intervention is critical to patient survival and neurological outcome.

There is, therefore, a need for devices and methods enabling objective, and intermittent or continuous evaluation of a subject's pupil size and/or pupillary reflex.

SUMMARY

The present disclosure relates to a device and methods for assessing the pupil size and/or pupillary reflex of a subject while the eyelids of the subject are closed.

Advantageously, this obviates the need for lifting the subject's eyelids to assess his pupil size and/or pupillary reflex, thereby increasing patient comfort and reducing labor requirements.

The device and methods, disclosed herein, may be partially or even fully automated; such that once the device is positioned on the patient, assessment of the pupil size and/or pupillary reflex may be performed requiring little or no further assistance from the medical staff. Advantageously, the reduced need for medical staff attendance enables frequent or even continuous measurements of the pupil size and/or pupillary reflex and may thus ensure that changes in the pupil size and/or pupillary reflex, indicative of a deterioration in the patient's neurological condition, are immediately identified, thereby significantly increasing the chances of survival as well as neurological outcome.

As a further advantage, the device and methods disclosed herein provide an objective and reproducible assessment of the subject's pupil size and/or pupillary reflex and changes therein, by evaluating quantifiable parameters, as further explained herein. This reduces or even eliminates the inaccuracies and inconsistencies characterizing today's manual assessment and enables reliably determining changes in the subject's pupil size and/or pupillary reflex, both as compared to previous measurements as well as to a patient specific baseline, e.g. pupil size at time of hospitalization or pupil size prior to surgery.

According to some embodiments, there is provided a device for pupil size and/or pupillary reflex assessment in a subject having closed eyelids, the device including one or more light sources configured to transmit light toward a vitreous cavity of the subject and one or more light detectors configured to detect light exiting the subject's pupils, through the closed eyelid.

According to some embodiments, the one or more light source may be a non-inductive light source (i.e. a light source transmitting light having a wavelength and/or intensity, which does not induce a pupillary reflex as further described hereinbelow). As a non-limiting example, the device may be used only to measure the pupil size without measuring pupil reflex. In such a situation the light source may be a non-inductive light source, which enables measuring the size of the pupil without inducing a change in said size.

According to some embodiments, the non-inductive light source may be configured to transmit infrared (IR) light, such as near IR (NIR) light in the range of 750 nm-1 mm. The IR light is preferably transmitted during the measuring of the pupil size (i.e. prior to inducing a pupillary reflex), as described in FIG. 13 below or during the entire procedure. According to some embodiments, the one or more light detectors may include an IR camera, sensitive to near-IR, configured to enable detection of the pupil contour and/or pupil shape by near-IR imaging. According to some embodiments, the device may further include an optical long pass filter (e.g. 800 nm) configured to reduce background light.

Additionally, or alternatively, the one or more light source may be an inductive light source, (i.e. a light source transmitting light having a wavelength and/or intensity, which induces a pupillary reflex as further described hereinbelow). As a non-limiting example, the device may be used to measure the change in pupil size—pupillary reflex by using an inductive light source. In such an embodiment, the light source induces a change in pupil size which is measured and compared either to standard pupil size or to an initial pupil size taken upon admittance of the patient.

According to some embodiments, the device may include both an inductive and a non-inductive light source. According to some embodiments, the device measures both initial pupil size by using a first, non-inducible light (that does not cause significant change in the pupil size) and in addition measures that pupil reflex change in pupil size by using a second inducible light.

According to some embodiments, the device may further include an inductive light source configured to transmit inductive light (light capable of inducing a pupillary reflex), i.e. in the range of 400-700 nm. The visible light is configured to be transmitted to the subject's eye(s), through the closed eyelid(s) and is configured to induce the pupillary reflex.

According to some embodiments, the device further includes a processor configured to receive the light detected by the light detector and/or the image from the imaging camera (e.g. IR camera or other imaging camera) and to determine the subject's pupil size, based on the received light intensity, based on detection/lack of detection of light, based on a change in light intensity which is correlative to changes in the light intensity of light transmitted, based on a speed of change in the received light intensity and/or based on image-analysis of the image(s) obtained from the IR camera (or other imaging camera). According to some embodiments, the image analysis may include applying segmentation algorithms to the image to extract the area and/or contour and/or shape of the pupil. As used herein the term "segmentation" may refer to the process of subdividing a digital image into multiple segments (set of pixels) having similar attributes. According to some embodiments, the segmentation may be based on discontinuity, i.e. portioning of the image based on identified abrupt changes. According to some embodiments, the segmentation may be based on similarity, i.e. portioning of the image based on similar regions according to predefined criteria, such as thresholding, region growing, region splitting and merging, etc. Each possibility is a separate embodiment. According to some embodiments, the segmentation may be performed in a horizontal, vertical and/or diagonal direction. Each possibility is a separate embodiment.

According to some embodiments, the light detection and/or imaging of the subject's pupils, pupil size and/or pupillary reflex may be performed separately for each pupil. According to some embodiments, the processor may be further configured to compare the detected light, the sizes of each of the subject's pupils and/or the pupillary reflex of each pupil.

According to some embodiments, the processor may be further configured to compare the determined pupil size and/or the pupillary reflex to a baseline intensity of light exiting the subject's pupils, a baseline pupil size and/or a baseline pupillary reflex. According to some embodiments, the baseline parameters may be parameters obtained in subjects having a normal pupillary reflex.

According to some embodiments, the processor may be further configured to compare the determined pupil size and/or the pupillary reflex to a previously determined pupil size and/or a previously determined pupillary reflex.

According to some embodiments, the processor may be further configured to compute a trend in the determined pupil size and/or in the pupillary reflex and changes therein.

According to some embodiments, the processor may be further configured to trigger an alarm if an abnormal pupil size and/or an abnormal pupillary reflex is detected.

According to some embodiments, the processor may be configured to determine the subject's pupil size and/or the pupillary reflex periodically and/or continuously.

According to some embodiments, the device includes a platform unit configured to be worn and/or positioned on the subject's head, such that at least part of the platform unit is positioned in front of the subject's eyes. According to some embodiments, the one or more inductive, and/or non-inductive light sources, and/or the one or more light detectors, and/or the one or more imaging cameras may be attached to the platform unit.

According to some embodiments, the one or more light sources may include at least two light sources positioned on the platform unit in such manner that light emitted by the two light sources is transmitted through the subject's temples, when the platform unit is worn and/or positioned on the subject's head.

According to some embodiments, the one or more light sources may be positioned on the platform unit, such that light is transmitted through the back of the subject's head, when the platform unit is worn and/or positioned on the subject's head.

According to some embodiments, the one or more light detectors may be positioned on the platform unit, such as to be placed in front of the subject's eyes, when the platform unit is worn and/or positioned on the subject's head.

According to some embodiments, the one or more light detectors may include a plurality of optical fibers.

According to some embodiments, the one or more light detectors may include or be an IR-camera sensitive to near-IR. According to some embodiments, the one or more light detectors may include or be a camera sensitive to light in the IR spectrum. According to some embodiments, the one or more light detectors may include or be a camera sensitive to light in the visual spectrum. According to some embodiments, the one or more light detectors may include or be a camera sensitive to light in the ultra-violet spectrum.

According to some embodiments, at least the part of the platform unit that is positioned in front of the subject's eyes may be made from a material impenetrable to light. According to some embodiments, the entire platform unit may be made from a material impenetrable to light.

According to some embodiments, the platform unit may be sized and shaped to prevent penetration of light.

According to some embodiments, there is provided a method for determining pupil size of a subject having closed eyelids, the method including transmitting light toward a vitreous cavity of the subject using one or more light sources; detecting, using a light detector, light exiting the subject's pupils, through the subject's closed eyelid(s).

By another embodiment the present invention concerns a method for determining change in pupil size in response to an inductive light, the method comprising transmitting inductive light through the subject's closed eyelid to the subject's eye, thereby inducing a pupillary reflex; and determining pupillary reflex functioning based on changes in the intensity of light exiting the subject's pupils.

By yet another embodiment the present invention concerns a method of determining both pupil size and pupil reflex of a subject having closed eyelids, the method comprising: transmitting non-inductive light toward the vitreous cavity of the subject; detecting, using a light detector, light exiting the subject's pupils through the subject's closed eyelid and/or determining the subject's pupil size based on an imaging of the subject's closed eye(s); transmitting inductive light through the subject's closed eyelid to the subject's eye, thereby inducing a pupillary reflex; transmitting light toward a vitreous cavity of the subject using one or more light sources; detecting, using a light detector, light exiting the subject's pupils, through the subject's closed eyelid and/or determining the subject's pupil size, based on an imaging of the subject's closed eye(s); and determining pupillary reflex functioning, based on a change in the determined pupil size before and after inducing the pupillary reflex.

According to some embodiments, the method further includes determining, using a processor, the subject's pupil size and/or pupillary reflex, based on the detected light and/or based on a speed of change in the received light intensity.

According to some embodiments, there is provided a method for determining pupil size of a subject having closed eyelids, the method including transmitting non-inductive light toward a vitreous cavity of the subject using one or more light sources; and imaging, using an IR camera, the subject's eye, through the closed eyelid, based on the transmitted non-inductive light. According to some embodiments, the method further includes transmitting inductive light through the subject's closed eyelid to the subject's eye, thereby inducing a pupillary reflex; transmitting non-inductive light toward the vitreous cavity of the subject; and imaging, using an IR camera, the subject's eye, through the closed eyelid, based on the transmitted non-inductive light. According to some embodiments, the method further includes determining, using a processor, the subject's pupil size and/or pupillary reflex, based on an image analysis on one or more images obtained from the imaging before and/or after inducing the pupillary reflex.

According to some embodiments, the method may further include comparing the sizes of each of the subject's pupils and/or the pupillary reflex of each pupil to one another.

According to some embodiments, the method may further include comparing the determined pupil size and/or the pupillary reflex to a baseline pupil size and/or a baseline pupillary reflex.

According to some embodiments, the method may further include comparing the determined pupil size and/or the pupillary reflex to a previously determined pupil size and/or pupillary reflex.

According to some embodiments, the method may further include computing a trend in the pupil size and/or in the pupillary reflex.

According to some embodiments, the method may further include triggering an alarm if an abnormal pupil size and/or an abnormal pupillary reflex is determined.

According to some embodiments, there is provided a system for intermittent and/or continuous determination of a pupil size and/or pupillary reflex of a subject having closed eyelids, the device comprising, an ultrasound transducer configured to provide ultrasound outputs of a subject's eye(s), through the eyelid(s), and a platform unit configured to be worn and/or positioned on the subject's head; wherein the ultrasound transducer is configured to be attached to the platform unit, such as to be positioned proximate to the subject's eyes.

According to some embodiments, the platform unit may be worn and/or positioned on the subject's head.

According to some embodiments, the platform unit may further include an inductive light source configured to transmit inductive light (light capable of inducing a pupillary reflex), i.e. light in the range of 400-700 nm. The visible light is configured to be transmitted to the subject's eye(s), through the closed eyelid(s) and to induce the pupillary reflex.

According to some embodiments, the system may further include a processor configured to determine the subject's pupil size based on the obtained ultrasound outputs.

According to some embodiments, the processor may be further configured to compare the sizes of each of the subject's pupils and/or the pupillary reflex of each pupil, based on the obtained ultrasound outputs.

According to some embodiments, the device may include two ocular ultrasound transducers configured simultaneously to provide ultrasound outputs for each of the subject's eyes.

According to some embodiments, the processor may be further configured to compare the determined pupil sizes and/or pupillary reflex to baseline pupil sizes and/or pupillary reflex and/or to previously determined pupil sizes and/or pupillary reflex.

According to some embodiments, the processor may be further configured to compute a trend in the pupil size and/or pupillary reflex.

According to some embodiments, the processor may be further configured to trigger an alarm if an abnormal pupil size and/or an abnormal pupillary reflex is determined.

According to some embodiments, the ultrasound transducer may be an ocular ultrasound transducer. According to some embodiments, the ocular ultrasound transducer may be configured to operate at a frequency of 10-60 MHz. As a non-limiting example for imaging of the anterior chamber, a frequency of about 20 MHz may be used in order to obtain images having a resolution suitable for image processing, however higher frequencies may provide higher spatial resolution in the near field. As another non-limiting example, for imaging of the posterior chamber, an average frequency of 10 MHz may be suitable for obtaining a resolution that enables image processing. Without being bound by any theory, the lower the frequency the deeper the ultrasonic beam will propagate and a better spatial resolution in the far field be achieved. It is understood that the exact frequency utilized may be defined based on the resolution required and/or the object (anterior/posterior chamber).

In addition to these ranges, other ranges may be of interest depending on the beam forming process used for image generation aiming to achieve image quality with focus in the area of interest.

According to some embodiments, the ultrasound transducer comprises one or more attachment elements, configured to attach said ultrasound transducer to an eye patch, configured to be placed on the subject's eye.

According to some embodiments, there is provided an eye patch for determination of a subject's pupil size, the patch having a first and a second sheath attached to each other so as to form a sac there between, and a conductive media contained within said sac.

According to some embodiments, the conductive media may be configured to allow ultrasound waves, transmitted by an ultrasound transducer positioned on the patch, to reach the subject's eye.

According to some embodiments, the patch may be sized and shaped to prevent ambient light from reaching the subject's eye. According to some embodiments, the patch may be shaped to fit the anatomy of human eyes.

According to some embodiments, the patch may include one or more attachment elements configured to secure ultrasound transducers to the patch.

According to some embodiments, the patch may include positioning markers configured to assist a positioning of the ultrasound transducers on the patch.

According to some embodiments, the patch may include a plurality of apertures allowing the conductive media to be released from the sac.

According to some embodiments, the patch may include an indicator configured to indicate a content of the conductive media within the sac.

According to some embodiments, there is provided a platform unit configured to be worn and/or positioned on the subject's head; the platform unit including an attachment element configured to allow attachment of an ocular ultrasound transducer, such that the ultrasound transducer be positioned proximate to the subject's closed eyelid, when the platform unit is worn and/or positioned on the subject's head.

According to some embodiments, at least a part of the platform unit, which is positioned in front of the subject's eyes, when the platform unit is worn and/or positioned on the subject's head, may be made from a material impermeable to light.

According to some embodiments, there is provided a method for determining pupil size and/or pupillary reflex of a subject having closed eyelids, the method including transmitting ultrasound to the subject's eye(s) through the eyelid (s) using an ultrasound transducer to obtain an ultrasound output; and determining the size of the subject's pupils, based on a measurement performed on the ultrasound output. According to some embodiments, the method further includes transmitting inductive light through the subject's closed eyelid to the subject's eye, thereby inducing a pupillary reflex; transmitting ultrasound to the subject's eye(s) through the eyelid(s) using an ultrasound transducer to obtain an ultrasound output; and determining the size of the subject's pupils and/or pupillary reflex based on a measurement performed on the ultrasound output obtained in response to inducing the pupillary reflex.

According to some embodiments, the method may further include comparing the sizes of the subject's pupils and/or the pupillary reflex of each pupil.

According to some embodiments, the method may further include comparing the determined pupil size and/or pupillary reflex to a baseline pupil size and/or pupillary reflex and/or to a previously determined pupil size and/or pupillary reflex.

According to some embodiments, the method may further include computing a trend in the pupil size and/or in the pupillary reflex.

According to some embodiments, the method may further include triggering an alarm if an abnormal pupil size and/or an abnormal pupillary reflex is determined.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1:
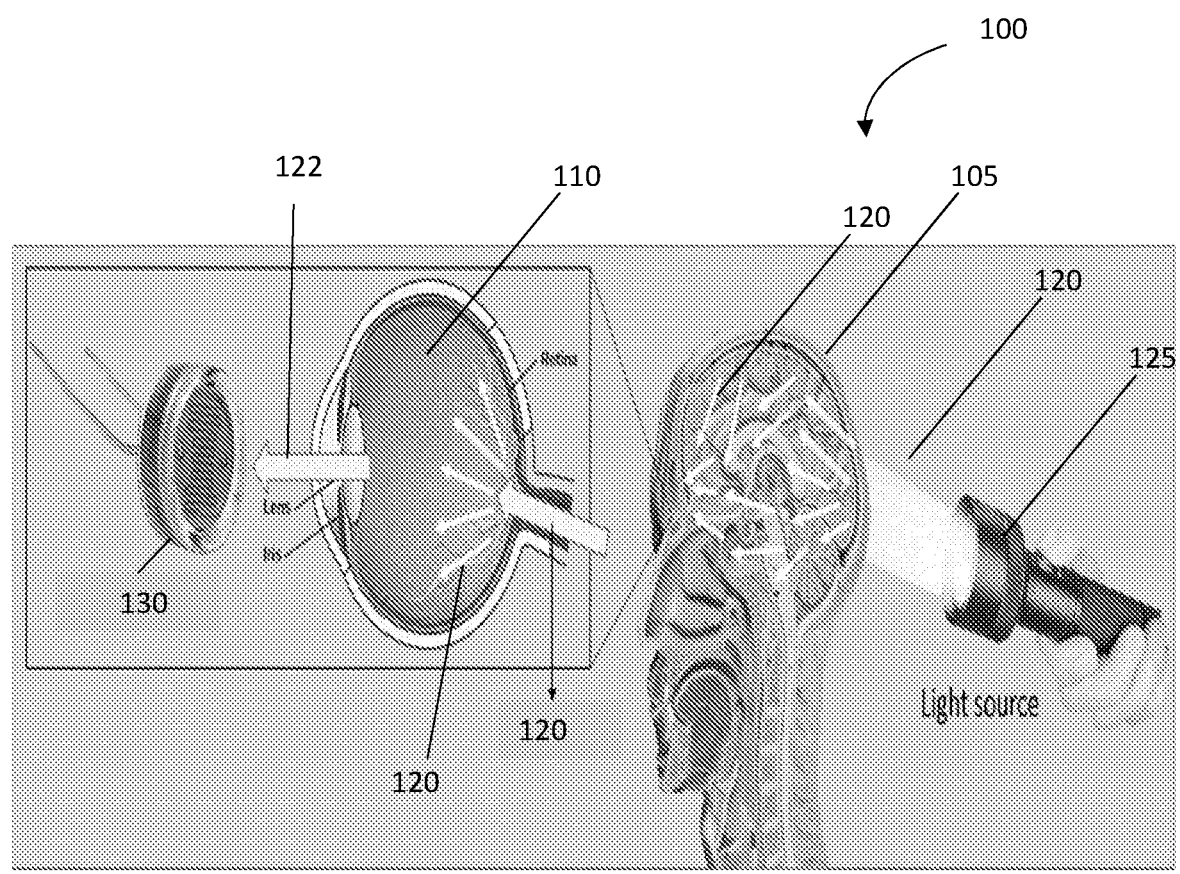
FIG. 1 illustratively depicts a method for assessing a subject's pupil size and/or pupillary reflex by detecting the intensity of trans-cranially transmitted light exiting the subject's pupils and/or time of change of the pupil's diameter, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

There is provided, according to some embodiments, a device for determining a pupil size and/or pupillary reflex of a subject, the device including one or more non-inductive light sources capable of transmitting light to or toward a vitreous cavity of the subject and one or more light detectors configured to detect an intensity and/or time to peak of light exiting the subject's pupils, through the subject's closed eyelid(s), determined in response to the transmitted light.

There is provided, according to some embodiments, a device for determining a pupil size and/or pupillary reflex of a subject, the device including one or more non-inductive light sources capable of transmitting light to or toward a vitreous cavity of the subject and one or more cameras configured to image the subject's eye(s) and/or pupil through the closed eyelid(s) based on the transmitted light. According to some embodiments, imaging the subject's eye may include imaging the subject's eye's posterior and/or anterior chamber.

As used herein, terms "subject" and "patient" may refer to any individual for which determining a pupil size and/or pupillary reflex is of medical relevance. According to some embodiments, the subject may be a head trauma patient, a subject undergoing brain surgery, patients with ischemic or hemorrhagic stroke/event, patients with encephalopathy following liver transplantation or surgeries; multiple trauma patients undergoing other surgeries such as fracture fixation, vascular repair, abdominal interventions; patients with brain infections; encephalopathy patients suffering from acute or chronic hepatic insufficiency/failure; encephalopathy following autoimmune processes involving brain vasculature or any other neurological condition.

As used herein the terms "pupil size" and "pupil diameter" may be used interchangeably and refers to the size/diameter of the hole located in the center of the iris of the eye that allows light to strike the retina. According to some embodiments, the determining of the pupil size may be performed in response to light being illuminated on the eye, also referred to herein as "pupillary light reflex". When bright light is illuminated on the eye, light sensitive cells in the retina, including rod and cone photoreceptors and melanopsin ganglion cells, will send signals to the oculomotor nerve, specifically the parasympathetic part coming from the Edinger-Westphal nucleus, which terminates on the circular iris sphincter muscle. When this muscle contracts, it reduces the size of the pupil. This is the pupillary light reflex, which is an important test of brainstem function. The normal pupil size in adults varies from 2 to 4 mm in diameter in bright light to 4 to 8 mm in the dark and is also known to vary between different individuals as well as with age.

Within the vertebrate eye, there are considered to be three chambers: anterior, posterior, and vitreous. The vitreous chamber is the largest of the three chambers and is located behind the lens and in front of the optic nerve. It is filled with a thick, clear gel-like substance called the vitreous humor.

According to some embodiments, the one or more light sources may be configured to emit light within the spectrum of near Infra-Red (IR) range, $\lambda$=about 700 to about 1500 nm or higher wavelengths. Each possibility is a separate embodiment. According to some embodiments, the one or more light sources may be configured to emit light within the range of 400-750, 650-1500 nm, 700-1400 nm, 750-1200 nm, 750-1000 nm, 800-1000 nm or any other suitable range. Each possibility is a separate embodiment. According to some embodiments, the one or more light sources may be configured to emit light at a wavelength and/or intensity, which does not affect the pupils' diameter, also referred to herein as "non-inductive light". According to some embodiments, the one or more light sources may be configured to emit light at a wavelength and/or intensity enabling its transmission through the subject's head to the vitreous cavity without heating or causing damage to surrounding tissue. According to some embodiments, the one or more light source may be an LED. According to some embodiments, the one or more light source may be a laser. According to some embodiments, the one or more light source may be a lamp.

According to some embodiments, the one or more light sources may be a single light source. According to some embodiments, the single light source may be capable of emitting light reaching the vitreous cavity of both the subject's eyes, either simultaneously or consecutively (for example due to movement of the light source relative to the patient's eyes). According to some embodiments, the device may include two light sources e.g. a first light source configured to transmit light to the right vitreous cavity from the right temple of the subject and a second light source configured to transmit light to the left vitreous cavity from the left temple of the subject. According to some embodiments, the device may include more than two light sources such as 3, 4, 5 or more light sources. Each possibility is a separate embodiment.

According to some embodiments, the one or more light sources may be an integral part of the device. Alternatively, the one or more light sources may be a separate element configured to be physically and/or functionally attached to the device.

As used herein, the term "light detector" may refer to any light detector capable of detecting light transmitted by the light source and exiting the subject's pupils. According to some embodiments, the one or more light detectors may be a single light detector. According to some embodiments, the light detector may be any light detector capable of detecting light at least in the range of 300 nm to 1000 nm or higher, such as 400 nm and higher, 550 nm and higher, or 750 nm and higher. Each possibility is a separate embodiment. According to some embodiments, the light detector may be a charge-coupled device (CCD). According to some embodiments, the light detector may be a complementary metal oxide semiconductor (CMOS). According to some embodiments, the single light detector may be configured to detect light exiting both of the subject's pupils, either simultaneously or consecutively (for example due to movement of the light detector relative to the patient's eyes). According to some embodiments, the light detector may include a plurality of optical fibers configured to convey the light exiting the subject's pupils to the light detector cell. According to some embodiments, the optical fiber may be a light pipe, a single mode and/or a multimode fiber, with or without filters. Each possibility is a separate embodiment. According to some embodiments, the one or more light detectors may refer to two light detectors, a first light detector configured to detect light exiting the right pupil and a second light detector configured to detect light exiting the left pupil. According to some embodiments, the one or more light detectors may include more than two light detectors, such as 3, 4, 5 or more light detectors. Each possibility is a separate embodiment. According to some embodiments, the light detector may include an array of light detectors, each array including a plurality of light detectors (e.g. more than 5, more than 10 or more than 20 light detectors—each possibility being a separate embodiment. As used herein, the term "array" with respect to the plurality of light detectors may refer to an arrangement of the light detectors, optionally systematically, in rows and columns. According to some embodiments, the device may include two arrays, each array positioned in front of one of the patient's eyes.

According to some embodiments, the one or more light detectors may be a camera such as, but not limited to, an IR camera. According to some embodiments, the IR camera may be sensitive to near IR light and be capable of performing NIR-imaging.

According to some embodiments, the one or more light detectors may be an integral part of the device. Alternatively, the one or more light detectors may be a separate element configured to be physically and/or functionally attached to the device.

According to some embodiments, the device may further include an inductive light source configured to transmit inductive light towards the subject's eye(s) through the closed eyelid(s). As used herein, the term "inductive light source" may refer to light capable of inducing a pupillary reflex. According to some embodiments, the inductive light source may be configured to transmit visible light, i.e. in the range of 400-700 nm, 400-750 nm, or 400-1000 nm Each possibility is a separate embodiment. According to some embodiments, the inductive light source may be configured to transmit light in the visible spectrum. According to some embodiments, the inductive light source may be configured to transmit light in the near-IR spectrum.

According to some embodiments, the one or more inductive light sources may be an integral part of the device. Alternatively, the one or more inductive light sources may be a separate element configured to be physically and/or functionally attached to the device.

According to some embodiments, the device further includes a processor configured to receive the detected light and/or image(s) from the one or more light detectors and to determine the subject's pupil size based on the detected light and/or the imaging.

According to some embodiments, the processor may be any computer, computing system, or similar electronic processing device that manipulates and/or transforms, processes, computes, calculates, determines, estimates the subject's pupil size and/or pupillary reflex based on the data received from the device, here light exiting the subject's pupils in response to light transmitted to the subject's vitreous cavities, speed of pupil diameter change and/or imaging of the subject's eye performed based on the non-inductive light transmitted through the vitreous cavities. According to some embodiments, determining the subject's pupil size and/or pupillary reflex may include determining the light intensity and/or speed of change in the received light intensity indicative and/or correlative to the subject's pupil size and/or pupillary reflex. Each possibility is a separate embodiment. According to some embodiments, determination of the subject's pupil size and/or pupillary reflex may be performed based on an image analysis performed on images obtained during the imaging of the subject's eye(s). According to some embodiments, the image analysis may include segmentation of the image using a segmentation algorithm configured to extract the area of the pupil and/or the contour and/or the shape of the pupil in the image. According to some embodiments, the image analysis may be automatic or semi-automatic.

According to some embodiments, the processor may be an integral part of the device. Alternatively, the processor may be a remote unit, such as a remote computer, a laptop, a smartphone or any other device having processing capabilities and which is configured to receive and process (through wires or wirelessly) data relating to the light intensity detected by the one or more light detectors and/or the imaging.

According to some embodiments, the pupil size and/or pupillary reflex may be determined separately/individually simultaneously or consecutively for each pupil. This enables detecting unequal pupil sizes, also referred to herein as "anisocoria", as well as asymmetry in speed of pupils' diameter change which may be indicative of ischemia, intracranial aneurysms, head trauma, and brain tumors or other conditions causing oculomotor nerve palsy.

According to some embodiments, the processor may be configured to determine the subject's pupil size and/or pupillary reflex periodically (i.e. every five minutes, every 10 minutes or any other suitable time interval) and/or continuously. It is understood that such continuous monitoring of the subject's pupil size is unfeasible using the currently known techniques, both because it would be highly labor intensive, but also due to the fact that the current method of pupil size and pupillary reflex evaluation requires the subject's eyelid to be open.

According to some embodiments, the processor may be further configured to compare the determined pupil size and/or pupillary reflex to a baseline pupil size and/or pupillary reflex and/or to a previously determined pupil size and/or pupillary reflex.

As used herein, the term "baseline", with regards to pupil size and/or pupillary reflex, may refer to a predetermined baseline pupil size and/or to a speed of diameter change, respectively, such as, but not limited, to a textbook normal pupil size and/or pupillary reflex, a textbook pupil size associated with a specific neurological condition, an average normal or disease specific pupil size and/or pupillary reflex determined based on a library of pupil sizes optionally gathered by the device and stored in a pupil size and/or pupillary reflex library. Each possibility is a separate embodiment. Additionally, or alternatively, the baseline pupil size and/or pupillary reflex may be a patient specific baseline pupil size and/or pupillary reflex. Advantageously, this may take into consideration that pupil sizes and/or pupillary reflex are known to vary between subjects and according to age. Moreover, a patient specific baseline may level out patient-specific characteristics, such as, but not limited to, non-pathological anisocoria (also known as physiological anisocoria), found in about 20% of normal people such as Adie's pupil phenomenon which is a result of internal ocular muscle denervation. According to some embodiments, the baseline pupil size and/or pupillary reflex may be manually determined as a predetermined baseline, a patient specific baseline or a combination of both. For example, for patients undergoing prescheduled neurological surgery, a patient specific baseline (or a combination of patient specific and predetermined baseline) may be more relevant and may serve as a tool for evaluating the progression and/or success of the surgery. On the other hand, for patients arriving at the hospital with head trauma, a patient specific baseline may be of limited relevance.

As used herein, the term "previously determined pupil size and/or pupillary reflex" may refer to a pupil size and/or pupillary reflex determined at an earlier point of measuring, such as 5 minutes before, 20 minutes before, 1 hour before or any other suitable time point prior to a current pupil size measurement. Additionally, or alternatively, the previously determined pupil size and/or pupillary reflex may refer to an average pupil size and/or pupillary reflex of the patient. According to some embodiments, the average pupil size and/or pupillary reflex may refer to an average of all the pupil sizes and/or pupillary reflex determined from the patient. Additionally, or alternatively, the average pupil size and/or pupillary reflex may refer to an average pupil size and/or pupillary reflex determined over a last predetermined period of time (such as, but not limited to, 5 min, 10 min, 1 hour or any other suitable period of time) prior to the current pupil size and/or pupillary reflex measurement, also referred to herein as "moving window" average. Advantageously, comparing the pupil size and/or pupillary reflex of the subject to the subject's previously determined pupil sizes and/or pupillary reflex may enable detection of pathological changes in the pupil size and/or pupillary reflex as it occurs and thus enable immediate, often life-saving medical intervention prior to an irreversible deterioration in the patient's condition.

According to some embodiments, the processor may be further configured to compute a trend in the subject's pupil size and/or pupillary reflex. Such trend may enable the medical staff to detect incremental, but significant changes in the subject's pupil size and/or pupillary reflex, which may be indicative of his/her neurological condition.

That is, the processor may be configured to determine the subject's neurological status based on the determined pupil size and/or pupillary reflex, the comparison of the size and/or pupillary reflex of the subject's pupils, the comparison of the pupil size and/or pupillary reflex to the baseline pupil size and/or pupillary reflex and/or to the previously determined pupil size and/or pupillary reflex, and/or on the computed trend in the pupil size and/or pupillary reflex. Each possibility is a separate embodiment.

According to some embodiments, the processor may be configured to trigger an alarm if a change in the subject's neurological status is determined According to some embodiments, the processor may be configured to trigger an alarm if a change in the subject's pupil size and/or pupillary reflex is detected. According to some embodiments, the alarm may be triggered if the pupil size and/or pupillary reflex has changed by more than 2%, 5%, 10% or any other suitable percentage. Each possibility is a separate embodiment. According to some embodiments, the alarm may be triggered if the pupil size is determined to be more than 3.5, more than 4 mm, more than 4.5 mm in bright light. According to some embodiments, the alarm may be triggered if the speed of pupils' diameter change is determined to be more than 0.5, 1, 1.5, 2 seconds in response to illumination with visible light. Each possibility is a separate embodiment. According to some embodiments, the alarm may be triggered if a less than 1%, 2/%, 5%, 10% or other suitable percentage change in the subject's pupil size is detected in response to a pupillary reflex test.

According to some embodiments, the processor may be further configured to provide a medical recommendation based on the determined pupil size and/or pupillary reflex and/or changes therein.

According to some embodiments, the processor may be further configured to increase/reduce the frequency of the pupil size measurement and/or pupillary reflex measurement based on a previously obtained pupil size measurement and/or pupillary reflex.

According to some embodiments, the device may further include a display configured to display the determined pupil size and/or pupillary reflex, the change in the determined pupil size and/or pupillary reflex as compared to a baseline and/or previous pupil size and/or pupillary reflex of the subject. According to some embodiments, the display may further display the neurological status of the patient, as determined based on the pupil size and/or pupillary reflex. According to some embodiments, the display may further display the medical recommendation provided in response to the determined pupil size, the determined pupillary reflex and/or changes therein. This may be of particular benefit in out-of-hospital settings, such as ambulances or triaging patients in the emergency room.

According to some embodiments, the display may be an integral part of the device. According to some embodiments, the display may be an integral part of the processor. According to some embodiments, the display may be a stand-alone display configured to be physically and/or functionally connected to the device. According to some embodiments, the display may be part of a general-purpose monitor or incorporated into monitors of other medical devices. Each possibility is a separate embodiment.

According to some embodiments, the device may include a platform unit configured to be worn and/or positioned on the subject's head, such that at least part of the platform unit is positioned in front of the subject's eyes. According to some embodiments, the one or more light sources and/or the one or more light detectors may be attached to the platform unit. As used herein, the term "platform unit" may refer to any element configured to be attached to or worn on the patient's head, such as, but not limited to, glasses, a net, a hood, a frame, or the like. Each possibility is a separate embodiment.

According to some embodiments, the one or more non-inductive light sources may be positioned on, molded on, attached to or otherwise mounted on the platform unit, such that light is transmitted through each of the subject's temples when in use or such that light is transmitted through the back of the subject's head when in use. According to some embodiments, the one or more non-inductive light sources may be positioned such that light is transmitted through the patient's mouth, nose or ears. Each possibility is separate embodiment. According to some embodiments, the one or more non-inductive light sources may be positioned such that light is transmitted through the sclera (the white area in the eye) and collected in front of the patient's, optionally closed, eyelids. Alternatively, the one or more non-inductive light sources may be attachable (and optionally also detachable) to the platform unit. For example, each non-inductive light source and/or the platform unit may include clips or other suitable attachment element configured to allow attachment between the non-inductive light source and the platform unit.

According to some embodiments, the non-inductive light source may get electricity either from an external power source or from a battery, attached to the platform unit.

According to some embodiments, the one or more light detectors may be positioned on, molded on, attached to or otherwise mounted on the platform unit, such as to be located in front of the subject's eyes when the platform unit is worn and/or positioned on the subject's head. Alternatively, the one or more light detectors may be attachable (and optionally also detachable) to the platform unit. For example, each light detector and/or the platform unit may include clips or other suitable attachment element configured to allow attachment between the light detector and the platform unit.

According to some embodiments, the one or more inductive light sources may be positioned on, molded on, attached to or otherwise mounted on the platform unit, such as to be located in front of the subject's eyes when the platform unit is worn and/or positioned on the subject's head. Alternatively, the one or more inductive light sources may be attachable (and optionally also detachable) to the platform unit. For example, each inductive light source and/or the platform unit may include clips or other suitable attachment element configured to allow attachment between the inductive light sources and the platform unit.

According to some embodiments, at least the part of the platform unit positioned in front of the subject's eyes may be made from a material impenetrable to light. This serves to ensure that light exiting the pupils will not escape the light detectors and/or to ensure that ambient light will not interfere with the measurement. As a non-limiting example, the platform unit may be glasses in which the lenses are made of a material impenetrable to light.

According to some embodiments, the platform unit may be sized and shaped to prevent penetration of light. As a non-limiting example, the platform unit may be glasses, which include side covers and/or light barriers made from a material impenetrable to light.

According to some embodiments, the platform unit may include one or more mechanisms (e.g. battery driven slides) allowing the one or more non-inductive light sources, the one or more light detectors and/or the one or more inductive light sources to move (e.g. to slide), from one eye to the other. Each possibility is a separate embodiment. Such sliding mechanism may enable utilizing a single non-inductive light source, a single light detector and/or a single inductive light source for examination of both eyes. According to some embodiments, the processor may be further configured to control the operation of the mechanism.

According to some embodiments, there is provided a method for determining pupil size and/or pupillary reflex of a subject having closed eyelids, the method comprising transmitting non-inductive light to or toward a vitreous cavity of the subject using one or more non-inductive light sources; detecting, using a light detector, the intensity of light transmitted by one or more light sources exiting the subject's pupils; and determining, using a processor, the subject's pupil size and/or pupillary reflex based on the received light intensity and recorded speed of change.

According to some embodiments, there is provided a method for determining pupil size and/or pupillary reflex of a subject having closed eyelids, the method comprising transmitting light to or toward a vitreous cavity of the subject using one or more light sources; imaging, using an imaging camera, of the subject's eye based on the transmitted non-inductive light; and determining, using a processor, the subject's pupil size based on the imaging. According to some embodiments, the method further includes transmitting inductive light towards the subject's eye(s) through the closed eyelid(s); whereafter the steps of transmitting non-inductive light to or toward the vitreous cavity of the subject, the imaging and the determining of the subject's pupil size are repeated. According to some embodiments, the method further includes determining the subject's pupillary reflex based on change in the subject's pupil size before and after transmitting the inductive light.

According to some embodiments, the pupil size and/or pupillary reflex may be determined simultaneously or consecutively for each pupil. According to some embodiments, the method may further include comparing the sizes and/or pupillary reflex of each of the subject's pupils. This enables detecting unequal pupil sizes, also referred to herein as "anisocoria", which may be indicative of ischemia, intracranial aneurysms, head trauma, and brain tumors or other conditions causing oculomotor nerve palsy, as essentially described herein.

According to some embodiments, as the method is performed while the subject's eyes are closed, the pupil size and/or pupillary reflex may be determined intermittently (i.e. every five minutes, every 10 minutes or any other suitable time interval) and/or continuously.

According to some embodiments, the method further includes comparing the determined pupil size and/or pupillary reflex to a baseline pupil size and/or pupillary reflex and/or to a previously determined pupil size and/or pupillary reflex, as essentially described herein.

According to some embodiments, the method may further include computing a trend in the subject's pupil size and/or pupillary reflex. Such trend may enable the medical staff to detect incremental but significant changes in the subject's pupil size and/or pupillary reflex, which may be indicative of his/her neurological condition, as essentially described herein.

According to some embodiments, the method may further include determining the subject's neurological status based on the determined pupil size, the comparison of the size of the subject's pupils, the comparison of the pupil size and/or pupillary reflex to the baseline pupil size and/or pupillary reflex and/or to the previously determined pupil size and/or pupillary reflex, and/or on the computed trend in the pupil size and/or pupillary reflex. Each possibility is a separate embodiment.

According to some embodiments, the method may further include triggering an alarm if a change in the subject's neurological status is determined According to some embodiments, the alarm may be triggered if a change in the subject's pupil size and/or pupillary reflex is detected. According to some embodiments, the alarm may be triggered if an abnormal pupil size is detected. Additionally, or alternatively, the alarm may be triggered if an abnormal pupillary reflex is detected. According to some embodiments, the alarm may be triggered if the pupil size has changed by more than 2%, 5%, 10% or any other suitable percentage. Each possibility is a separate embodiment. According to some embodiments, the alarm may be triggered if the pupil size is determined to be more than 3.5, more than 4 mm, more than 4.5 mm in bright light. Each possibility is a separate embodiment. According to some embodiments, the alarm may be triggered if a less than 1%, 2/%, 5%, 10% or other suitable percentage change in the subject's pupil size is detected in response to a pupillary reflex test.

According to some embodiments, the method may further include providing a medical recommendation based on the determined pupil size and/or change therein. According to some embodiments, the method may further include displaying the determined pupil size and/or pupillary reflex, the change in the determined pupil size and/or pupillary reflex as compared to a baseline and/or previous pupil size and/or pupillary reflex of the subject. Each possibility is a separate embodiment. According to some embodiments, the method may further include displaying the neurological status of the patient, and/or the medical recommendation on the display.

According to some embodiments, there is provided a device for intermittent and/or continuous determination of a pupil size and/or pupillary reflex of a subject having closed eyelids, the device comprising, an ultrasound transducer (e.g. an ocular ultrasound transducer) configured to provide ultrasound outputs of a subject's eyes and a processor configured to receive the ultrasound outputs and to determine the subject's pupil sizes based on the obtained ultrasound outputs.

According to some embodiments, the device may further include an inductive light source configured to transmit inductive light towards the subject's eye(s) through the closed eyelid(s). As used herein, the term "inductive light source" may refer to light capable of inducing a pupillary reflex. According to some embodiments, the inductive light source may be configured to transmit visible light, i.e. in the range of 400-750 nm or 400-700 nm.

According to some embodiments, the one or more inductive light sources may be an integral part of the device. Alternatively, the one or more inductive light sources may be a separate element configured to be physically and/or functionally attached to the device.

According to some embodiments, the processor may be further configured to determine the subject's pupillary reflex by comparing pupil sizes before and after inducing the pupillary reflex.

According to some embodiments, the ultrasound transducer may be configured to automatically or semi-automatically "search for" the pupil during imaging. This may advantageously allow imaging of pupils which are not forward directed (e.g. looking to the side). As a non-limiting example, the ultrasound transducer may include a two-dimensional (2D) probe configured to obtained images from more than one angle. As another non-limiting example, the device or the ultrasound transducer may (additionally or alternatively) include a mechanism configured to move the probe such that the pupil is properly imaged. According to some embodiments, the mechanism may be automatic or semi-automatic. According to some embodiments, the movement of the mechanism may be predetermined in which case subsequent image processing may "choose" images including the probe. According to some embodiments, the movement of the mechanism may be responsive, i.e. be determined based on an image pre-processing configured to identify whether the subject's pupil is in frame or not, whereafter the subsequent image analysis is performed on in-frame images only.

According to some embodiments, the ultrasound output may be an ultrasound image. According to some embodiments, the ultrasound output may be an ultrasound video. According to some embodiments, the ultrasound output may be an ultrasound signal.

According to some embodiments, the ultrasound transducer may be an ocular ultrasound transducer. As used herein, the terms "extraocular ultrasound transducer", "ocular ultrasound probe" and "ocular ultrasound transducer" may be used interchangeably and refer to any ultrasound device configured to provide ultrasound images/videos/signals of the eye when placed on the closed eyelid, and enabling the determination of the anatomical dimensions of the ocular anterior and posterior chambers. According to some embodiments, optional parameters, which may be evaluated using the ultrasound transducer, include the subject's pupil size, iris size, iris recess angle, optic nerve dimensions, retinal thickness and any other internal or external ocular muscle or part as well as speed of diameter change. Each possibility is a separate embodiment. According to some embodiments, the ultrasound transducer may facilitate functional analysis of the pupil.

Non-limiting examples of suitable ultrasonic transducers include A-Scan ultrasound transducers, B-Scan ultrasound transducers, Ultrasound Bio-microscopes and any other ocular ultrasound transducer capable of scanning objects at a depth of up to 60 mm. The transducers can be standard wire based and/or wearable and/or wireless or any other kind of transducer. They can be of size small or standard. The transducers may be built using sonocrystals or any other acoustic ultrasound sensors, such as capacitive micromachine ultrasound transducers (CMUTs), manufactured in-house or by any available vendor \manufacturer such as Micro Medical Devices (MMD). Any suitable amount of standard water-soluble ultrasound transmission gels may be used. According to some embodiments, the probes may be composed of a linear array of sensors or of a convex array of sensors or any other array structure, which allows a transmit-receive program/configuration. According to some embodiments, the ultrasound transducer may be configured to provide still images and/or signals and/or videos. According to some embodiments, the ultrasound transducer may be configured to operate at a frequency of more than 2 MHz, about 2-4 MHz or 4-6 MHz or 6-8 MHz or 8-10 MHz, or 10-12 MHz, or 12-15 MHz or 18-20 MHz, 10-60 MHz, 20-60 MHz, 30-60 MHz, 40-50 MHz or 50 MHz or any other suitable frequency or range of frequencies. According to some embodiments, the scanning depth may be fixed and/or adjustable. According to some embodiments, the transducers may be connected to any computer-based system and/or tablet and/or smartphone based systems or any other connection formats. According to some embodiments, the transducers may be connected using wires or wireless connections including all available wireless connections.

According to some embodiments, the processor may be configured to measure, extract, determine or otherwise extrapolate at least one pupil parameter from the ultrasound image/video, by applying an algorithm hereon.

According to some embodiments, the signals received from the transducer may be analyzed automatically or semi automatically to detect spatial or temporal signal variation, peak detection, gradient variation detection and/or any other signal-processing algorithm According to some embodiments, machine and/or deep learning based algorithms may be used in addition to or instead of spatial or temporal point detection, and/or signal and/or image classification and/or object detection and classification.

According to some embodiments, the analysis of the ultrasound output may be signal, image or video based analysis:

According to some embodiments, the algorithm may be automatic or semiautomatic.

According to some embodiments, semi-automatic algorithms may require a user input of one, two, or more anatomical markers on one, two, or more image/frame out of the entire scan, for example two markers pointing out the iris recess. Then, the iris may be segmented, the pupil detected and/or its dimensions measured. According to some embodiments, the analysis may be done using a same frame and subsequently tracking the feature detected in following frames, if available.

According to some embodiments, automatic algorithms may detect anatomical markers at first, and then detect and segment the iris and the pupil to measure the exact dimensions. Tracking and detection of the pupil in subsequent frames may likewise be performed.

According to some embodiments, the algorithm may utilize any segmentation and\or object detection based algorithm, while utilizing spatial and/or temporal features and information. Additionally, or alternatively, machine learning and deep learning based algorithms may be utilized for object detection and/or for computer-aided diagnosis.

According to some embodiments, the device may include two extraocular ultrasound transducers. As used herein, the term "two" with regards to ultrasound transducers may refer to an ultrasound unit including two ultrasound probes positioned on or attached to the unit so as to enable bilateral ultrasonic imaging. Alternatively, the term may refer to two separate extraocular transducers.

According to some embodiments, the processor may be any computer, computing system, or similar electronic processing device capable of manipulating, transforming, processing, computing, calculating, determining, or estimating the subject's pupil size, and/or pupillary reflex based on ocular ultrasound outputs (e.g. ultrasound images, videos and/or signals). According to some embodiments, the processor may be an integral part of the device. Alternatively, the processor may be a remote unit, such as a remote computer, a laptop, a smartphone or any other device having processing capabilities and which is configured to receive (through wires or wirelessly), process and/or perform measurements on the ocular ultrasound outputs.

According to some embodiments, the processor may be further configured to compare the sizes of the subject's pupils and/or pupillary reflex based on the obtained ultrasound outputs. According to some embodiments, the pupil size and/or pupillary reflex may be determined simultaneously or consecutively for each pupil. This enables detecting unequal pupil sizes, also referred to herein as "anisocoria", as well as asymmetric light reactivity, which may be indicative of ischemia, intracranial aneurysms, head trauma, and brain tumors or other conditions causing oculomotor nerve palsy. As used herein, the term asymmetric light reactivity may refer to an at least 5% difference, at least 10% difference, or at least 20% difference in light reactivity between the pupils. Each possibility is a separate embodiment.

According to some embodiments, the processor may be configured to determine the subject's pupil size and/or pupillary reflex periodically (i.e. every five minute every 10 minutes or any other suitable time interval) and/or continuously. It is understood that such continuous monitoring of the subject's pupil size is unfeasible using the currently known techniques both because it would be highly labor intensive, but also due to the fact that the current method of pupil size and/or pupillary reflex evaluation requires the subject's eyelid to be open.

According to some embodiments, the processor may be further configured to compare the determined pupil size and/or pupillary reflex to a baseline pupil size and/or pupillary reflex and/or to a previously determined pupil size and/or pupillary reflex, as essentially described herein.

According to some embodiments, the processor may be configured to determine the subject's neurological status based on the determined pupil size and/or pupillary reflex, the comparison of the size and/or pupillary reflex of the subject's pupils, the comparison of the pupil size and/or pupillary reflex to the baseline pupil size and/or pupillary reflex and/or to the previously determined pupil size and/or pupillary reflex, and/or on the computed trend in the pupil size and/or pupillary reflex, as essentially described herein. Each possibility is a separate embodiment.

According to some embodiments, the processor may be configured to trigger an alarm if a change in the subject's neurological status is determined, as essentially described herein. According to some embodiments, the processor may be configured to trigger an alarm if a change in the subject's pupil size and/or pupillary reflex is detected. According to some embodiments, the alarm may be triggered if an abnormal pupil size is detected. Additionally, or alternatively, the alarm may be triggered if an abnormal pupillary reflex is detected. According to some embodiments, the alarm may be triggered if the pupil size has changed by more than 2%, 5%, 10% or any other suitable percentage. Each possibility is a separate embodiment. According to some embodiments, the alarm may be triggered if the pupil size is determined to be more than 3.5, more than 4 mm, more than 4.5 mm in bright light. Each possibility is a separate embodiment. According to some embodiments, the alarm may be triggered if a less than 1%, 2/%, 5%, 10% or other suitable percentage change in the subject's pupil size is detected in response to a pupillary reflex test. According to some embodiments, the alarm may be triggered if the speed of pupils' diameter change is determined to be more than 0.5, 1, 1.5, 2 seconds in bright light. According to some embodiments, the alarm may be triggered if a trend in the pupil size and/or pupillary reflex is indicative of an enlargement of the subject's neurological status.

According to some embodiments, the processor may be further configured to provide a medical recommendation based on the determined pupil size and/or pupillary reflex and/or change therein, as essentially described herein.

According to some embodiments, the device may further include a transmitter configured to transmit the data (raw data as well as pupil size and light reactivity).

According to some embodiments, the device may further include a display configured to display the determined pupil size and/or pupillary reflex, the change in the determined pupil size and/or pupillary reflex as compared to a baseline and/or previous pupil size and/or pupillary reflex of the subject. According to some embodiments, the display may further display the neurological status of the patient, as determined based on the pupil size and/or pupillary reflex. According to some embodiments, the display may further display the medical recommendation obtained, provided in response to the determined pupil size, the determined pupillary reflex and/or changes therein. This may be of particular benefit in out-of-hospital settings, such as ambulances or triaging patients in the emergency room.

According to some embodiments, the display may be an integral part of the device. According to some embodiments, the display may be an integral part of the processor. According to some embodiments, the display may be a stand-alone display configured to be physically and/or functionally connected to the device. According to some embodiments, the display may be part of a general-purpose monitor or incorporated into monitors of other medical devices. Each possibility is a separate embodiment.

According to some embodiments, the device further includes a platform unit configured to be worn and/or positioned on the subject's head such that at least part of the platform unit is positioned in front of the subject's eyes.

According to some embodiments, the ocular ultrasound transducer may be positioned on, molded on, attached to or otherwise mounted on the platform unit, attached to the platform unit, such as to be positioned proximate to the subject's eyes when the platform unit is worn and/or positioned on the subject's head. Alternatively, the ocular ultrasound transducer may be attachable (and optionally also detachable) to the platform unit. For example, the ocular ultrasound transducer and/or the platform unit may include clips or other suitable attachment element configured to allow attachment between the ocular ultrasound transducer and the platform unit. As a non-limiting example, the platform unit may be a pair of glasses including elements, for example, on each of the lenses or in place of the lenses, configured to allow secure positioning and/or attachment of the ultrasound transducers.

According to some embodiments, the one or more inductive light sources may be attachable (and optionally also detachable) to the platform unit. For example, the inductive light source and/or the platform unit may include clips or other suitable attachment element configured to allow attachment between the light source and the platform unit. According to some embodiments, the one or more inductive light sources may be a single light source configured to transmit light to both the subject's eyes, either simultaneously or consecutively (for example, due to movement of the light source relative to the subject's eyes). Alternatively, the device may include two light sources each positioned in front of one of the subject's eyes, enabling bilateral pupil analysis.

According to some embodiments, the ocular ultrasound probe may include one or more attachment elements, configured to allow its attachment to an eye patch placed on the subject's eyes. According to some embodiments, the attachment elements may ensure that the probe is positioned correctly on the patient's eye. According to some embodiments, the attachment elements may serve to ensure that an interface is created between the probe and the patient's eye allowing ultrasonic imaging, while avoiding unnecessary pressure on the patient's eye.

According to some embodiments, the platform unit may include a mechanism (e.g. a battery driven slide, allowing the inductive light source to move, e.g. to slide, from one eye to the other, thereby enabling utilization of a single light source for the examination of both eyes. According to some embodiments, the processor may be further configured to control the operation of the mechanism.

According to some embodiments, there is provided an eye patch used for determination of a subject's pupil size and/or pupillary reflex. The patch may include a first and a second sheath attached to each other so as to form a sac there between, and a conductive media contained within said sac, the conductive media configured to allow ultrasound waves, transmitted by an ultrasound probe positioned on the patch, to reach the subject's eye.

As used herein, the terms "eye patch" and "eye pad" is a piece of material configured to be worn/positioned in front of a subject's eyes. According to some embodiments, the patch may be made from cloth. According to some embodiments, the patch may be made from a polymeric material. According to some embodiments, the patch may be made from a material nonabsorbent to liquids, such as water, saline or gels used for ultrasound. According to some embodiments, the patch may be attached around the head of a subject, for example, by an elastic band, a string, an adhesive bandage, a plastic device, which is clipped to a pair of glasses or any other suitable wearable feature. Each possibility is a separate embodiment.

As used herein, the term "sac" may refer to a compartment formed between two layers of the patch. The sac may be configured to contain a liquid configured to serve as a conductive media for ultrasonic imaging. According to some embodiments, the sac may be made of a material impermeable to liquids. According to some embodiments, the sac may be made of a material which does not absorb liquids. According to some embodiments, the sac may be made in different shapes to prevent liquid drain and leakage. According to some embodiments, the sac may be attached to a device configured to pump drained liquids and flow them back to the sac. According to some embodiments, the same pump may be attached to sacs of both eyes, or alternatively, one or more pumps may be used for each sac. Additional flexible material, such as, but not limited to, rubber may be used to prevent liquid drain or leakage. According to some embodiments, the flexible material may be attached to the pump device and/or to the sac.

As used herein, the term "conductive media" may refer to any media configured to provide optimal contact between an ultrasound probe and a subject's skin. According to some embodiments, the conductive media may be devoid of air bubbles when contained in the sac of the eye patch, so as to ensure optimal sound transmission. According to some embodiments, the conductive media may be water, alcohol, hydrogel, lipogels or any other suitable medium allowing transmission of ultrasonic waves or combination thereof. Each possibility is a separate embodiment. According to some embodiments, the conductive media is a hydrogel.

According to some embodiments, the patch may be sized and shaped to prevent ambient light to reach the subject's eye. According to some embodiments, the patch may be shaped to fit the anatomy of human eyes.

According to some embodiments, the patch may include one or more attachment elements configured to secure an ultrasound probe to the patch. According to some embodiments, the patch may include positioning markers configured to assist in positioning the ultrasound probe on the subject's eye, so as to facilitate the determining of the subject's pupil size. According to some embodiments, the attachment elements may serve to ensure that an interface is created between the probe and the patient's eye allowing ultrasonic imaging, while avoiding unnecessary pressure on the patient's eye.

According to some embodiments, the patch may include a plurality of apertures allowing the conductive media to be released from the sac. According to some embodiments, the apertures may be sized and shaped to release an amount of conductive media providing optimal imaging.

According to some embodiments, the patch may include an indicator configured to indicate a content of the conductive media within the sac. The indicator may thus serve to ensure that the ultrasound imaging is performed under optimal conditions during the entire monitoring session. According to some embodiment, the indicator may be a color indicator or other indicator, which is readily visible by the human eye or by a suitable reader.

According to some embodiments, there is provided a method for determining pupil size and/or pupillary reflex of a subject having closed eyelids, the method including transmitting ultrasound to a subject's eye using an ocular ultrasound probe to obtain an ultrasound output (e.g. ultrasound image, video and/or signal) determining the size of each of the subject's pupils, based on a measurement performed on the ultrasound output, as essentially described herein.

According to some embodiments, the method further includes transmitting inductive light through the subject's closed eyelid to the subject's eye, thereby inducing a pupillary reflex; transmitting ultrasound to the subject's eye(s) through the eyelid(s) using an ocular ultrasound transducer to obtain an ultrasound output; and determining the size of the subject's pupils and/or pupillary reflex based on a measurement performed on the ultrasound output obtained in response to inducing the pupillary reflex.

According to some embodiments, the method further includes comparing the sizes of the subject's pupils as well as light reactivity, as essentially described herein.

According to some embodiments, as the method is performed while the subject's eyes are closed, the pupil size may be determined intermittently (i.e. every five minute every 10 minutes or any other suitable time interval) and/or continuously. Each possibility is a separate embodiment.

According to some embodiments, the method further includes comparing the determined pupil size and/or pupillary reflex to a baseline pupil size and/or pupillary reflex and/or to a previously determined pupil size and/or pupillary reflex, as essentially described herein.

According to some embodiments, the method further includes computing a trend in the pupil size and/or pupillary reflex, as essentially described herein.

According to some embodiments, the method further includes determining the subject's neurological status based on the determined pupil size and/or pupillary reflex, the comparison of the size of the subject's pupils, the comparison of the pupil size and/or pupillary reflex to the baseline pupil size and/or pupillary reflex and/or to the previously determined pupil size and/or pupillary reflex; and/or on the computed trend in the pupil size and/or pupillary reflex, as essentially described herein. Each possibility is a separate embodiment.

According to some embodiments, the method further includes triggering an alarm if a change in the subject's neurological status is determined. According to some embodiments, the alarm may be triggered if a change in the subject's pupil size and/or pupillary reflex is detected. According to some embodiments, the alarm may be triggered if the pupil size has changed by more than 2%, 5%, 10% or any other suitable percentage. Each possibility is a separate embodiment. According to some embodiments, the alarm may be triggered if the pupil size is determined to be more than 3.5, more than 4 mm, more than 4.5 mm in bright light. Each possibility is a separate embodiment. According to some embodiments, the alarm may be triggered if a less than 1%, 2/%, 5%, 10% or other suitable percentage change in the subject's pupil size is detected in response to a pupillary reflex test. According to some embodiments, the alarm may be triggered if the speed of pupils' diameter change is determined to be more than 0.5, 1, 1.5, 2 seconds in bright light.

According to some embodiments, the method may further include providing a medical recommendation based on the determined pupil size and/or change therein. According to some embodiments, the method may further include displaying the determined pupil size, the change in the determined pupil size as compared to a baseline and/or previous pupil size of the subject. Each possibility is a separate embodiment. According to some embodiments, the method may further include displaying the neurological status of the patient, and/or the medical recommendation on the display.

Reference is now made to FIG. 1, which illustratively depicts a method 100 for assessing a subject's pupil size and/or pupillary reflex by detecting the intensity of trans-cranially transmitted light exiting the subject's pupils, according to some embodiments and/or by imaging the subject's eye based on the trans-cranially transmitted light. It is understood that the trans-cranially transmitted light preferably does not induce a pupillary reflex. As shown, a light 120 may be transmitted through a subject's head 105 toward a vitreous cavity 110 using a light source, here illustratively depicted as a stick light 125. Light source 125 is here shown to transmit light through the back of the subject's head; however, other configurations, such as light being transmitted through the temples or through the side of the subject's eyes (proximally to the outer V of the eye), are also applicable and within the scope of this disclosure. The transmitted light will subsequently exit the subject's pupils (as indicated by an arrow 122) where it can be detected by a light detector 130 and/or be imaged by an imaging camera. The intensity of the detected light may then be conveyed to a processor (not shown) configured to determine the subject's pupil size based on the detected light, as described herein.

Figure 2:
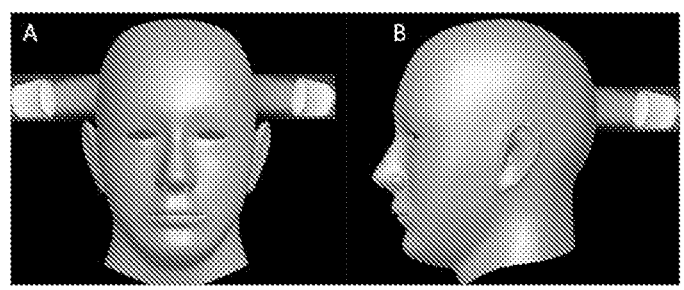
FIG. 2 shows optional directions of light transmission suitable for the assessment of the subject's pupil size and/or pupillary reflex as essentially described in FIG. 1.

Reference is now made to FIG. 2, which shows optional directions of light transmission suitable for the assessment of the subject's pupil size and/or pupillary reflex, as essentially described in FIG. 1. As shown in the left panel (panel A), light may be transmitted to the vitreous cavity from the side of the patient's head (through the temples or through the side of the eye, i.e. in proximity to the outer V of the eye). Alternatively, light may be transmitted to the vitreous cavity from the back of the patient's head, as shown in the right panel (panel B).

Figure 3:
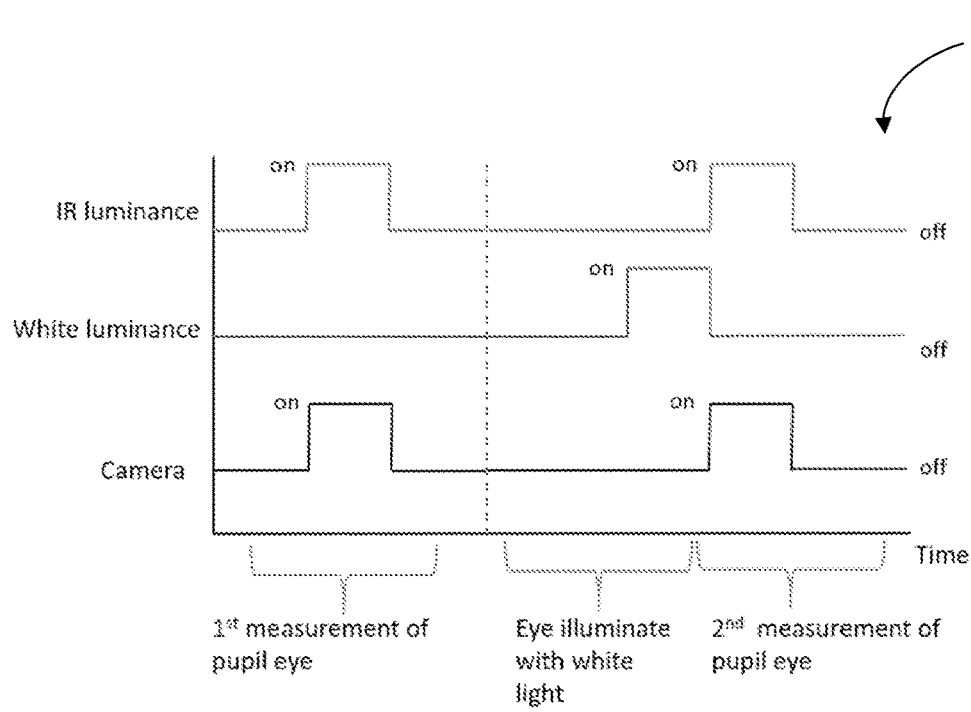
FIG. 3 shows a time line of a typical procedure for assessing a subject's pupil size and/or pupillary reflex.

Reference is now made to FIG. 3, which shows a time line 300b of a typical procedure for assessing a subject's pupil size and/or pupillary reflex. Three main time points can be identified, namely a) prior to inducing a pupillary reflex during which a first measurement of pupil size is performed; b) a period during which the pupillary reflex is induced; and c) post induction of the pupillary reflex during which a second measurement of pupil size is performed. During the first period (a) an initial pupil size may be determined, for example, by comparing to a baseline/range representing a normal baseline. Such determination alone may be indicative of a neurological status. For example, an abnormally large pupil size may be indicative of neurological dysfunction. During the first measurement, the non-inductive light source, such as a light source transmitting near-IR light, is activated. Due to the transmitting of the non-inductive light, the light detector, here an IR camera sensitive to near IR radiation, may be able to image the subject's eye and to determine the area and/or contour and/or shape of the subject's pupil by applying image analysis algorithms, such as, but not limited to, image segmentation algorithms. During the period of pupillary reflex induction (b), an inductive light source is activated, which light source preferably emits light in the visible range, as essentially described herein. During this period, no measurements of pupil size are performed, i.e. the non-inductive light source and the camera are turned off. Alternatively, measurements performed during this period may be subsequently discarded from further analysis. During the last period (c) the pupil size may be reassessed. By comparing the pupil size obtained before and after induction of the pupillary reflex, the normality/abnormality of the reflex may be determined. As before, during the second measurement, the non-inductive light source is once again activated thus enabling imaging of the subject's eye and determination of the area and/or contour and/or shape of the subject's pupil as essentially described. The activation of the non-inductive IR light source is here shown to be simultaneous with the operation of the IR camera at specific time points. It is, however, understood that the IR light source and/or the camera may be continuously activated throughout the entire procedure or parts thereof, whereafter image processing is used to identify the relevant measurements. It is further understood that the procedure may be performed on both eyes (either simultaneously or sequentially) thereby enabling the detection of differences in pupil size and/or pupillary reflex between the subject's eyes and its associated indications, as essentially described herein.

Figure 4:
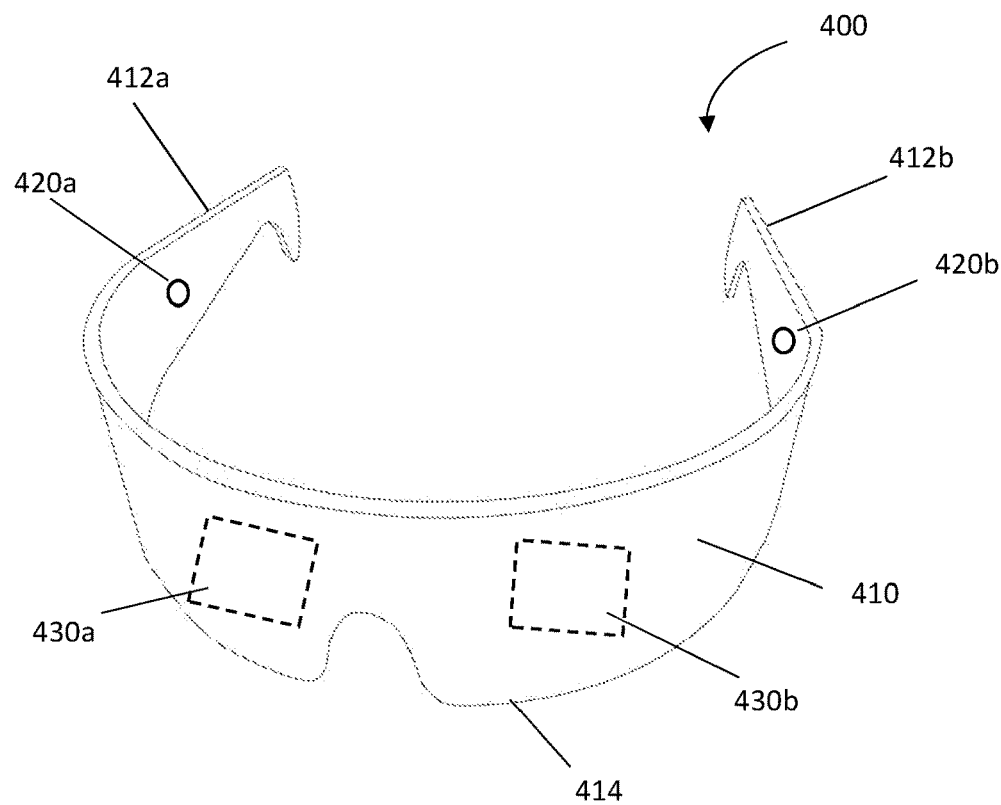
FIG. 4 shows a device for determining a pupil size and/or pupillary reflex of a subject suitable for detecting the intensity of trans-cranially transmitted light exiting a subject's pupils, according to some embodiments.

Reference is now made to FIG. 4, which shows a device 400 for detecting the intensity of trans-cranially transmitted light exiting a subject's pupils, according to some embodiments. Device 400 includes a platform unit here illustrated as eyeglasses 410. Eyeglasses 410 include frame temples 412a and 412b and a frame front 414. Each of frame temples 412a and 412b include a light source, here depicted as light sources 420a and 420b configured to transmit light through the side of a subject's head to the vitreous cavity, as essentially shown in FIG. 2. Frame front 414 is made from a material impermeable to light and includes light detectors 430a and 430b positioned such as to be located in front of the subject's eyes, when in use. Light detectors 430a and 430b are configured to detect the light exiting the subject's pupils as a result of the light transmitted by light sources 420a and 420b, as essentially described herein.

Figure 5A:
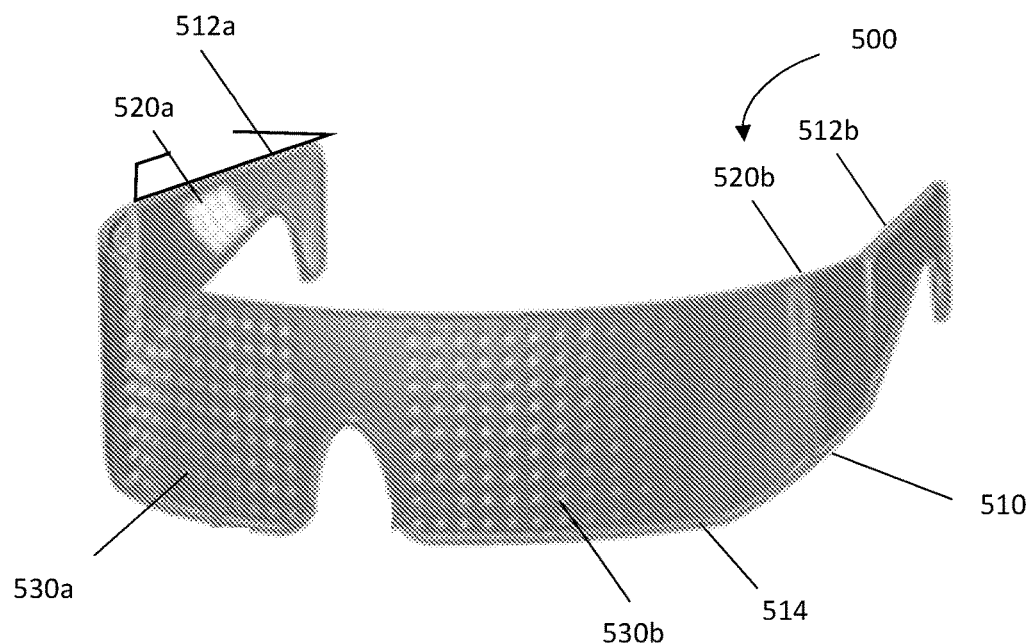
FIG. 5A shows a front view of a device for determining a pupil size and/or pupillary reflex of a subject suitable for detecting the intensity of trans-cranially transmitted light exiting a subject's pupils, according to some embodiments.
Figure 5B:
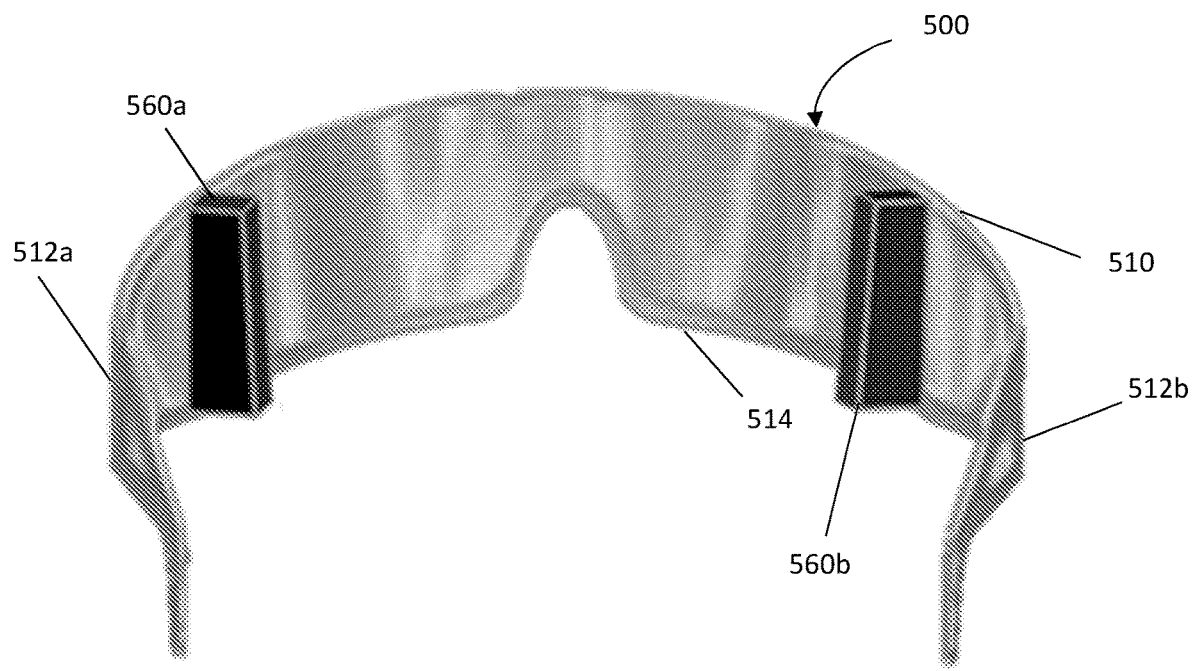
FIG. 5B shows a hind view of a device for determining a pupil size and/or pupillary reflex of a subject suitable for detecting the intensity of trans-cranially transmitted light exiting a subject's pupils, according to some embodiments.

Reference is now made to FIG. 5A and FIG. 5B, which show front and hind views of an exemplary device 500 for detecting the intensity of trans-cranially transmitted light exiting a subject's pupils, according to some embodiments. Device 500 includes a platform unit here illustrated as eyeglasses 510. Eyeglasses 510 include frame temples 512a and 512b and a frame front 514. Each of frame temples 512a and 512b include two light sources, here depicted as light sources 520a and 520b configured to transmit light through the side of a subject's head to the vitreous cavity, as essentially shown in FIG. 1. A frame front 514 is made from a material impermeable to light and includes light detector arrays 530a and 530b positioned such as to be located in front of the subject's eyes, when in use. Light detector arrays 530a and 530b are configured to detect the light exiting the subject's pupils in response to light transmitted by light sources 520a and 520b, as essentially described herein. Frame temples 512a and 512b further include light barriers 560a and 560b configured to prevent ambient light from reaching light detector arrays 530a and 530b as well as to prevent light exiting the subject's pupils to escape light detector arrays 530a and 530b.

Figure 6:
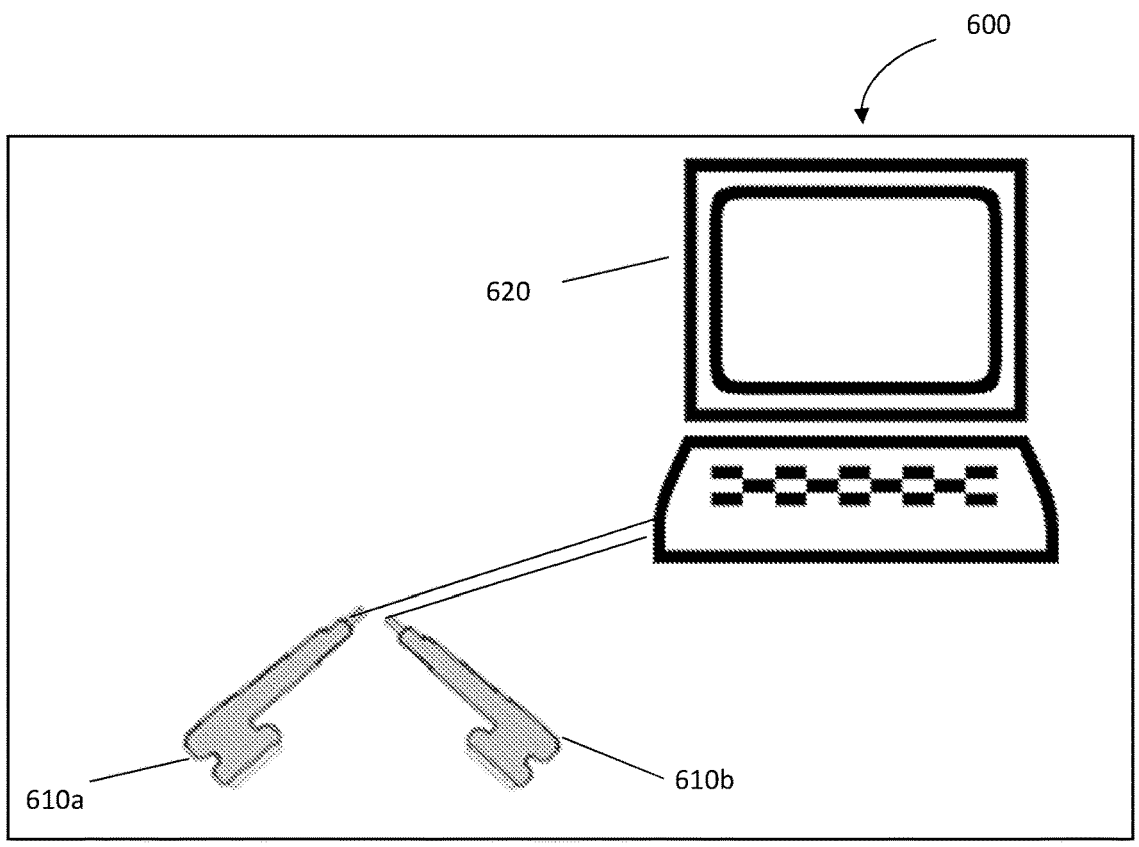
FIG. 6 shows a system for determining a pupil size and/or pupillary reflex of a subject comprising two ocular ultrasound transducers, according to some embodiments.

Reference is now made to FIG. 6, which shows a system 600 for determining a pupil size of a subject, according to some embodiments. System 600 includes two ocular ultrasound transducers 610a and 610b, configured to provide ultrasound outputs for a subject's eyes, and a processor 620, configured to determine the subject's pupil sizes, based on the obtained ultrasound outputs, as further described herein. Transducers 610a and 610b may be configured for attachment to a platform unit, as further described in FIG. 7 below.

Figure 7:
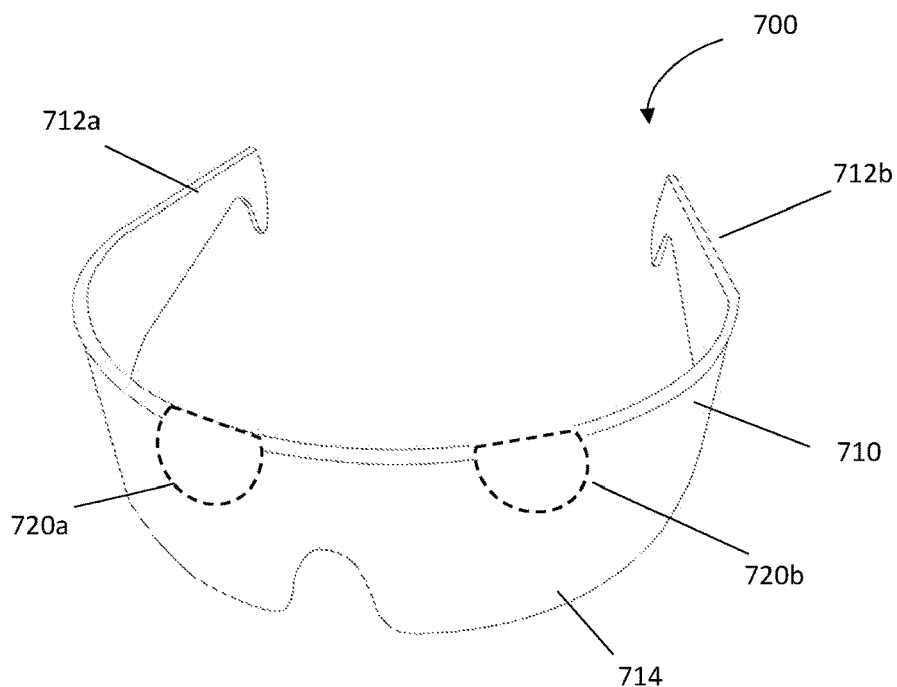
FIG. 7 shows a device for determining a pupil size and/or pupillary reflex of a subject by ultrasonic imaging, according to some embodiments.

Reference is now made to FIG. 7, which shows a device 700 for determining a pupil size of a subject by ultrasonic imaging, according to some embodiments. Device 700 includes a platform unit, here illustrated as eyeglasses 710. Eyeglasses 710 include frame temples 712a and 712b and a frame front 714. Frame front 714 is made from a material impermeable to light and includes attachment elements 720a and 720b, configured to allow attachment of ultrasonic transducers (not shown). Attachment elements 720a and 720b are positioned on frame front 714 in such manner that the ultrasonic transducers contact the subject's eyelids (or a patch positioned on the subject's eyelids), when in use.

Figure 8:
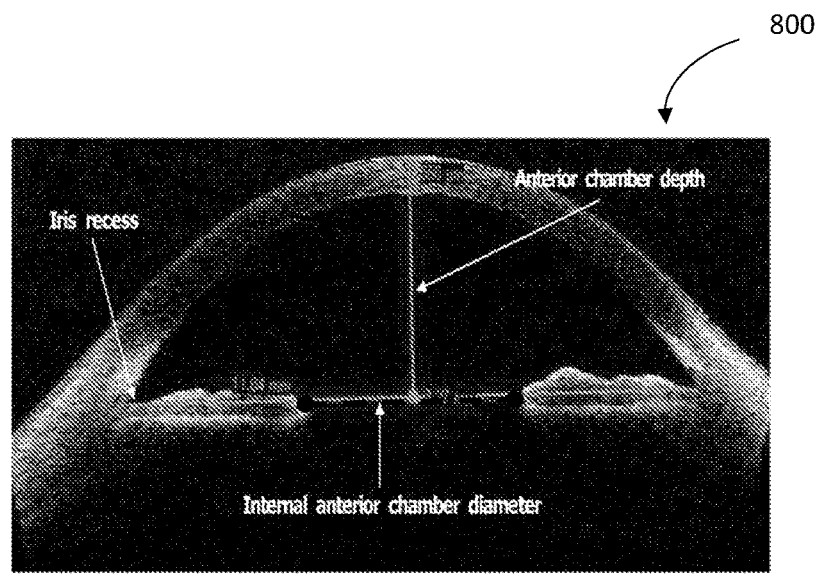
FIG. 8 is an illustrative example of an ocular ultrasound image; according to some embodiments.

Reference is now made to FIG. 8, which is an illustrative example of an ocular ultrasound image 800, according to some embodiments, obtained by utilizing an ocular transducer, as essentially described herein. Line 810 indicates the size of the pupil, as measured on image 800. The pupil size is calculated by determining the distance between the irises in each eye, also referred to herein as "internal anterior chamber diameter".

Figure 9:
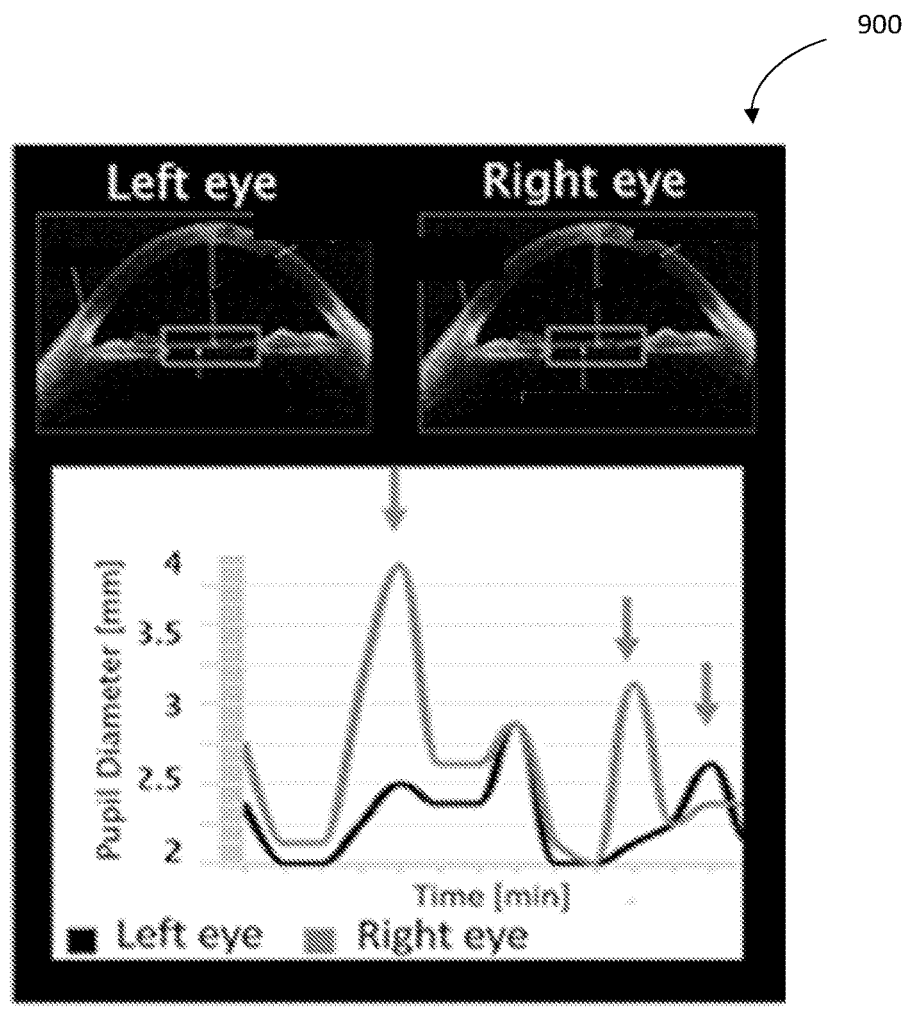
FIG. 9 is an illustrative example of an ocular ultrasound image; according to some embodiments.

Reference is now made to FIG. 9, which is an illustrative example of an ocular ultrasound output 900 comparing the sizes of a subject's right and left pupils according to some embodiments. After a baseline is set for each pupil, every following measurement is compared to the baseline and recorded in a graph. If one pupil, or both, are different from the baseline, the monitor will respond, for example by triggering an alarm.

Figure 10:
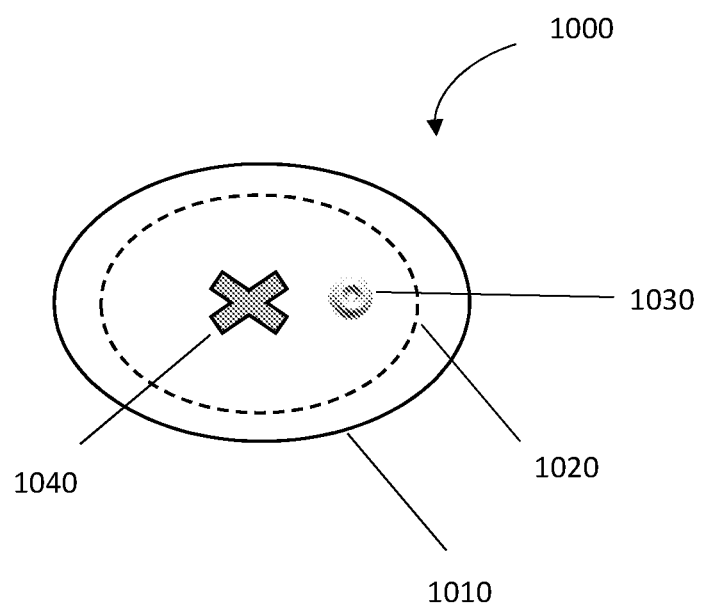
FIG. 10 is an illustrative example of an eye patch, according to some embodiments.

Reference is now made to FIG. 10, which is an illustrative example of an eye patch 1000, according to some embodiments. Eye patch 1000 includes a double-layered material 1010 forming a sac 1020, configured to contain conductive media allowing ultrasound waves, transmitted by an ultrasound transducer (not shown), positioned on eye patch 1000, to reach the subject's eye. Eye patch 1000 is here illustrated as being round but is preferably shaped according to the anatomy of human eyes and so as to prevent ambient light from reaching the subject's eye. Patch 1000 may include one or more attachment elements, configured to secure an ultrasound transducer (not shown) to the patch, here illustratively depicted as attachment element 1030. Attachment element 1030 may serve to ensure that an interface is created between the probe and the patient's eye allowing ultrasonic imaging, while avoiding unnecessary pressure on the patient's eye. Patch 1000 further includes a positioning marker 1040 configured to assist in positioning an ultrasound probe (not shown) on the subject's eye.

Figure 11:
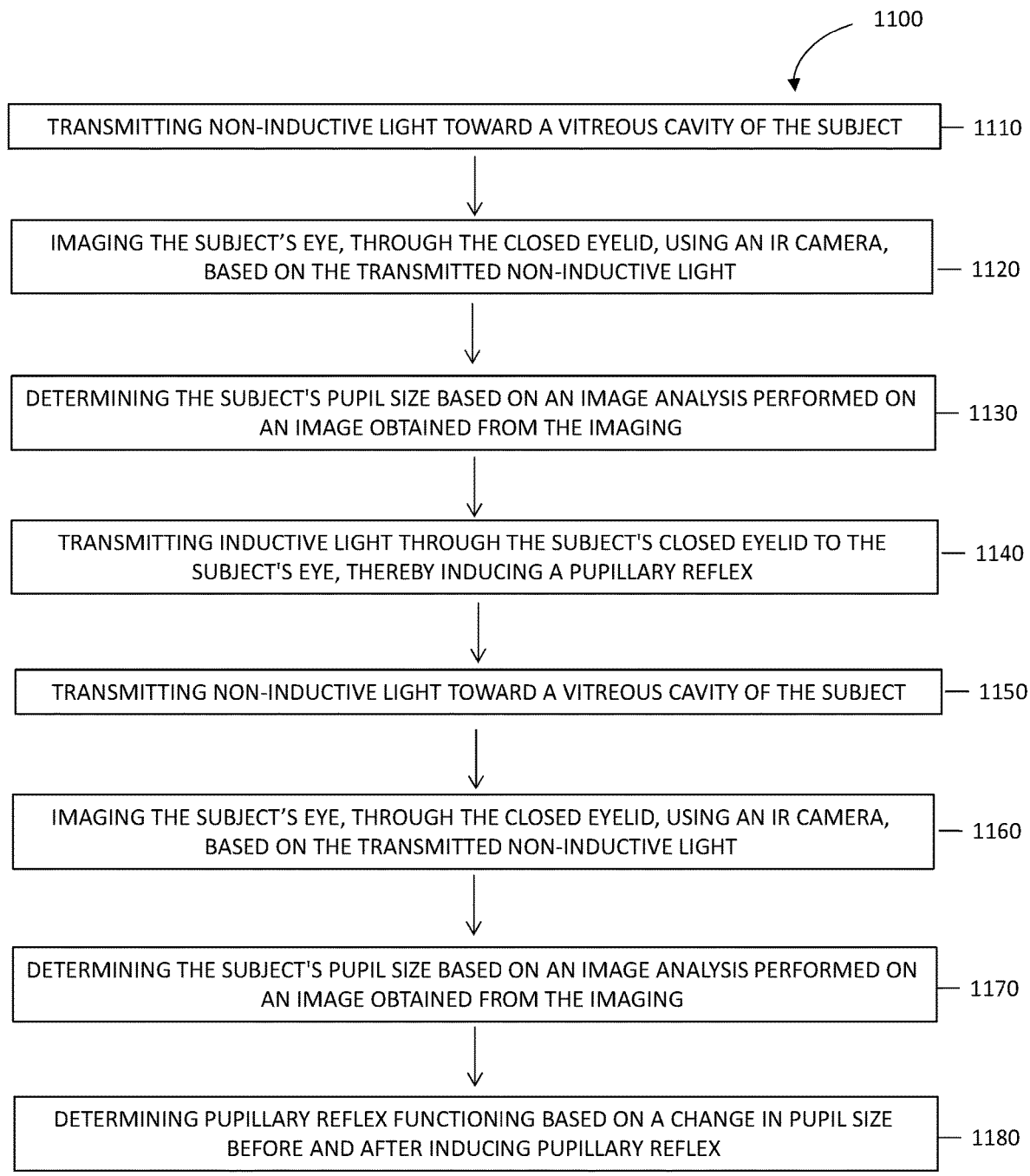
FIG. 11 is an illustrative flowchart of the method for assessing a subject's pupil size using transcranial illumination, according to some embodiments.

Reference is now made to FIG. 11, which is an illustrative flowchart 1100 of the method for assessing a subject's pupil size using transcranial illumination, according to some embodiments. In step 1110 of the method, non-inductive light is transmitted toward a vitreous cavity of the subject. While the non-inductive light source is turned on, the subject's eye is imaged, through the closed eyelid, using an IR camera, based on the transmitted non-inductive light (step 1120). In step 1130 the subject's pupil size is determined based on an image analysis performed on at least one image obtained from the imaging of step 1120. Optionally, the method further includes step 1140 in which inductive light is transmitted through the subject's closed eyelid to the subject's eye, thereby inducing a pupillary reflex; followed by transmitting non-inductive light toward the vitreous cavity of the subject (step 1150); and imaging, using a IR camera, the subject's eye, through the closed eyelid, based on the transmitted non-inductive light (step 1160). Optionally, the method further includes a step 1170 in which the pupil size after pupillary reflex induction, is determined based on an image analysis performed on at least one image obtained from the imaging of step 1160. Similarly, once the pupil sizes before and after inducing the pupillary reflex have been obtained, pupillary reflex functioning may optionally be determined, based on the obtained change in pupil size (step 1180).

Figure 12:
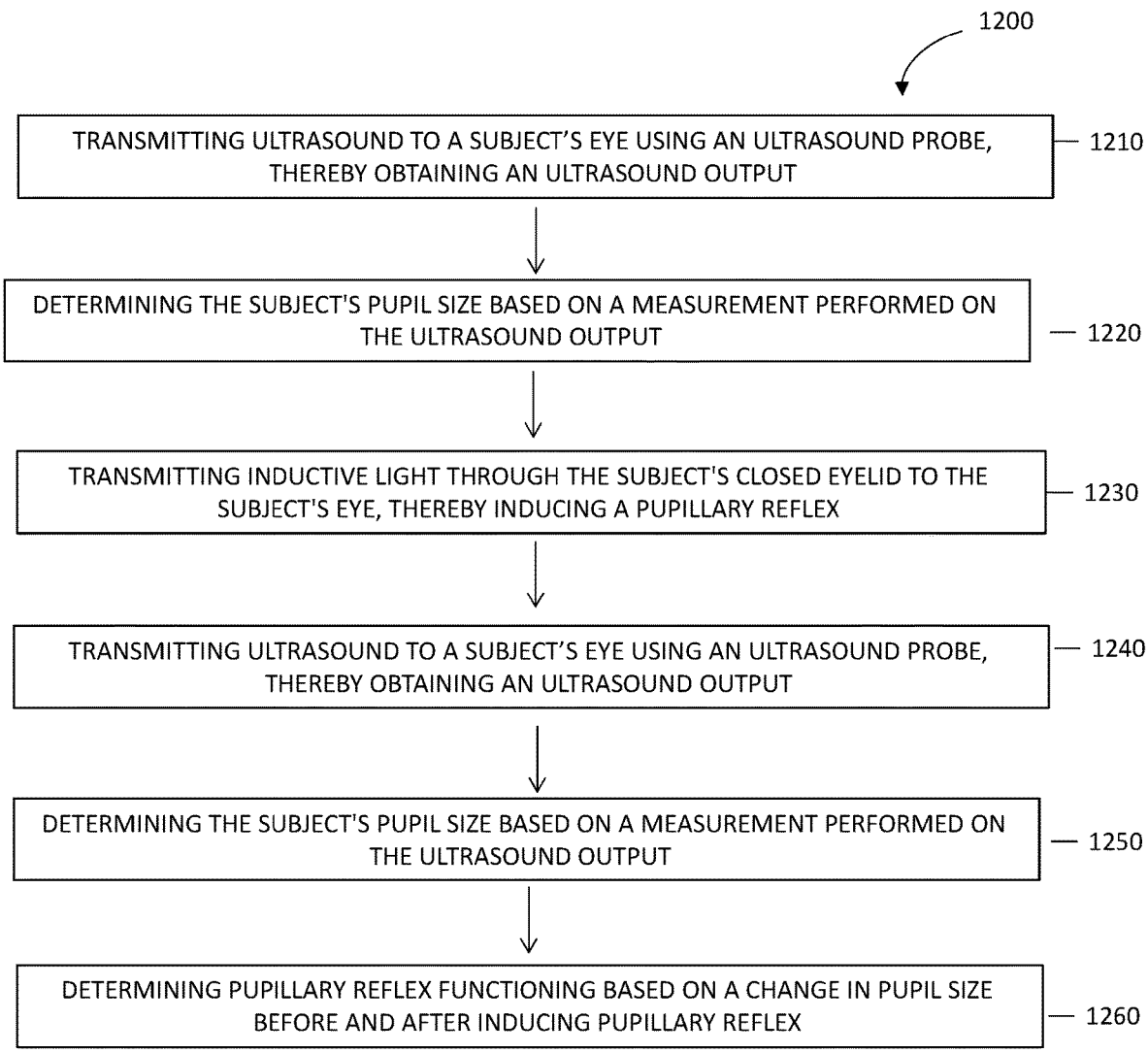
FIG. 12 is an illustrative flowchart of the method for assessing a subject's pupil size using ultrasound, according to some embodiments.

Reference is now made to FIG. 12, which is an illustrative flowchart 1200 of the method for assessing a subject's pupil size using ultrasound, according to some embodiments. In step 1210 of the method, ultrasound is transmitted to a subject's eye using an ocular ultrasound probe, thereby obtaining an ultrasound output (e.g. ultrasound image, video and/or signal). In step 1220 the subject's pupil size is determined based on a measurement performed on the ultrasound output of step 1210. Optionally, the method further includes step 1230 in which inductive light is transmitted through the subject's closed eyelid to the subject's eye, thereby inducing a pupillary reflex; followed by ultrasound imaging of the subject's eye (step 1240) and pupil size determination based on a measurement performed on the ultrasound output of step 1240 (step 1250). Once the pupil sizes before and after inducing the pupillary reflex have been obtained, pupillary reflex functioning may be determined, based on the obtained change in pupil size (step 1260).

EXAMPLES

Example 1—Ex-Vivo Determination of Pupil Size by Imaging

An ex-vivo experiment for measuring pupil size was performed on a swine eye. The swine eye was isolated and placed on a designated holder. The eye was illuminated from the side using LED light having a spectrum centered around 810 nm A digital camera sensitive to the near-IR range was used to image the eye from the front (pupil side), and an optical long pass filter (800 nm) was used to reduce background light. The pupil size was initially determined with on open eyelid and subsequently repeated with a closed eyelid. The measurements obtained for both scenarios were compared in order to determine the ability and the accuracy of pupil size determination with closed eyelids. An image-analysis segmentation algorithm was used to extract the area and contour of the pupil in each image, as essentially described herein. The derived contours were added (bold line) to the raw images to delineate the pupil.

Figure 13:
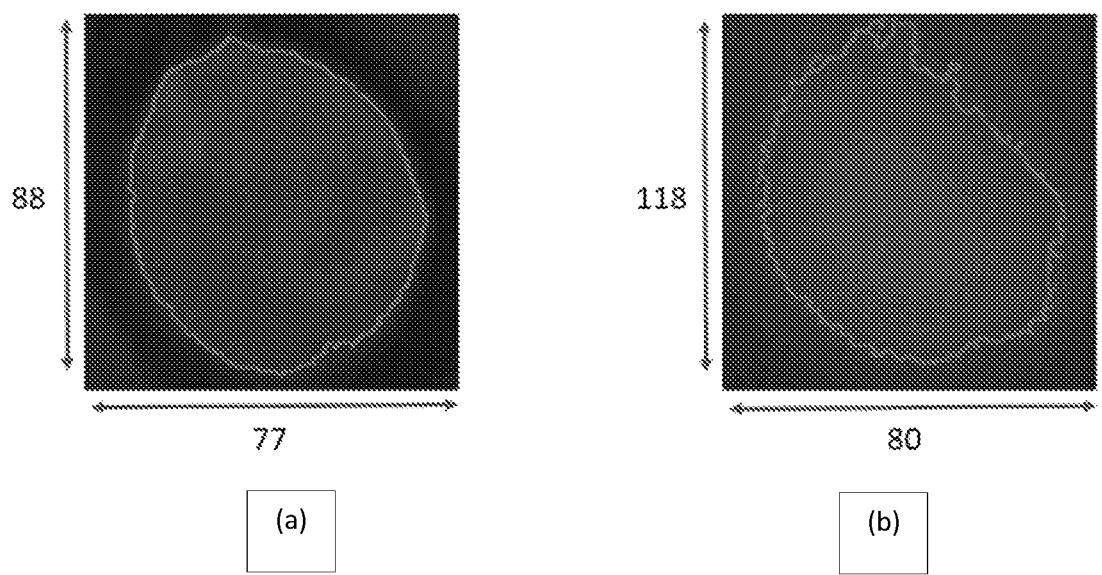
FIG. 13 shows images obtained in an ex-vivo assessment of pupil size using imaging.

FIG. 13 shows the images obtained with the pupil contour delineated thereon (the dimensions units of all pictures are pixels). The left panel (image a) shows the image and pupil contour obtained with on open eyelid. The right panel (image b) shows the image and pupil contour obtained with a closed eyelid.

As seen from FIG. 13 and from Table 1 below, setting forth the dimensions of the pupil shapes obtained, this experiment demonstrated the ability of the herein disclosed method to accurately assess the pupil dimension through a closed eyelid.

TABLE 1

| | pupil dimension | | |
|---|---|---|---|
| | Area [pixel$^2$] | Major Axis Length [pixel] | Minor Axis Length [pixel] |
| Swine without eyelid | 5415 | 88.8 | 77.9 |
| Swine with eyelid | 5427 | 118.7 | 80.3 |

Example 2—Determination of Pupil Size by Ultrasound

Figure 14A:
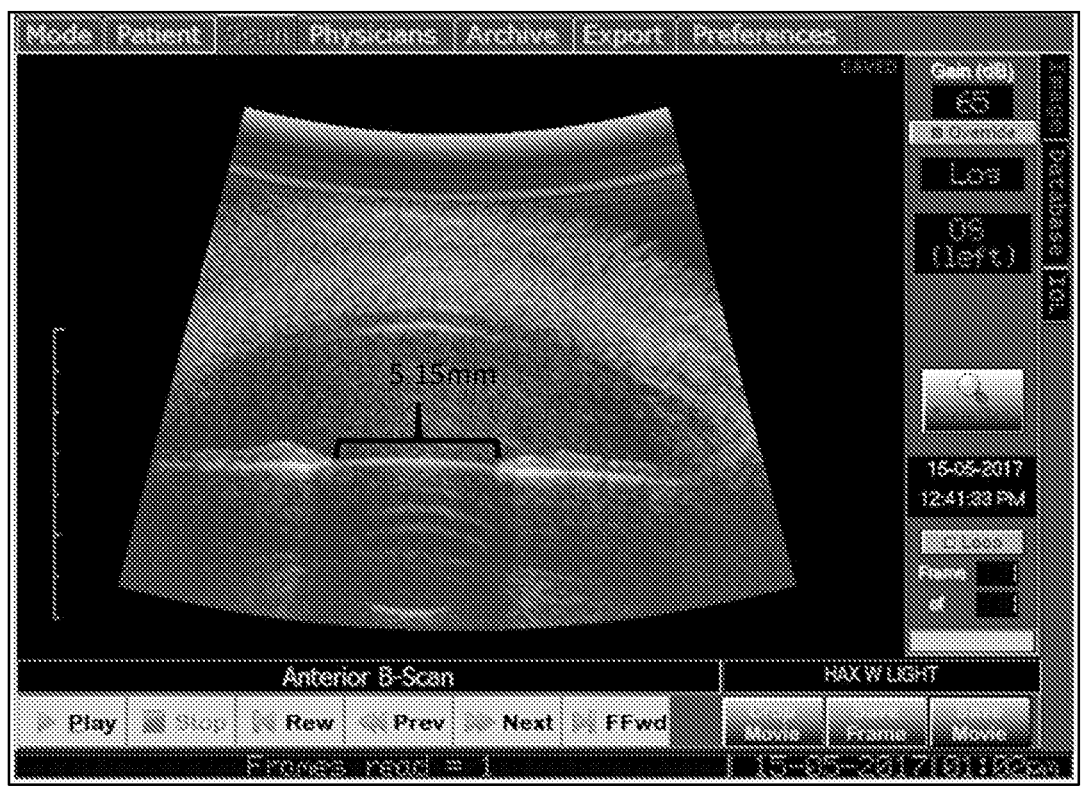
FIG. 14A shows a representative ultrasound image of a subject's eye, when looking forward.
Figure 14B:
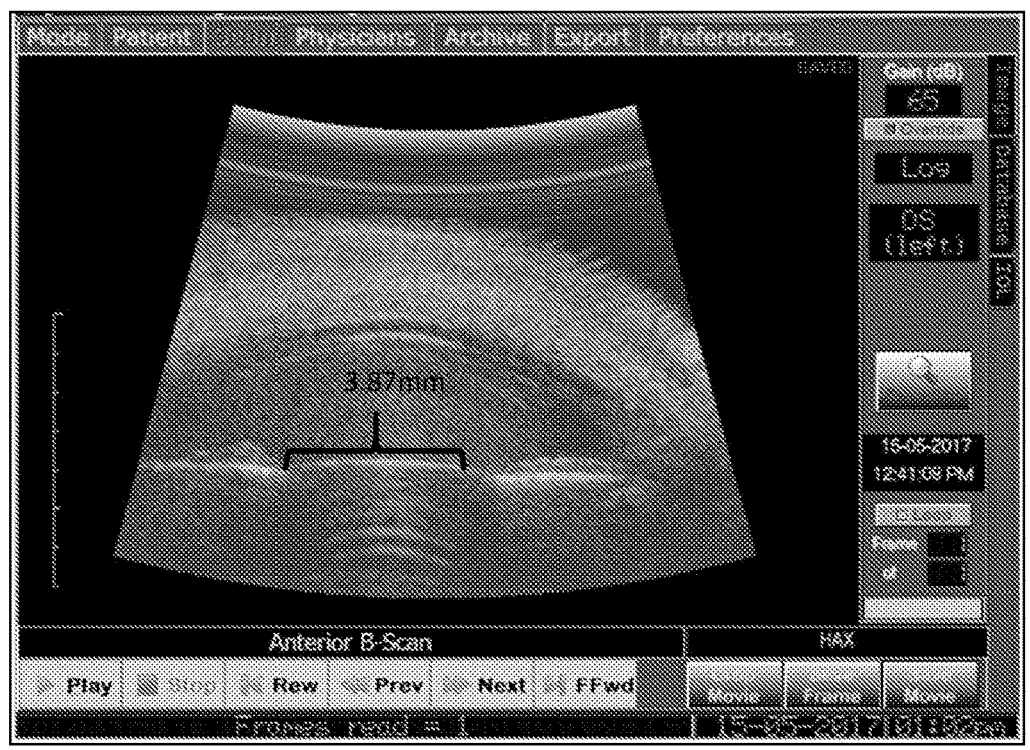
FIG. 14B shows a representative ultrasound image of the subject's eye, when looking forward (as in FIG. 14A) after inducing pupillary reflex.
Figure 14C:
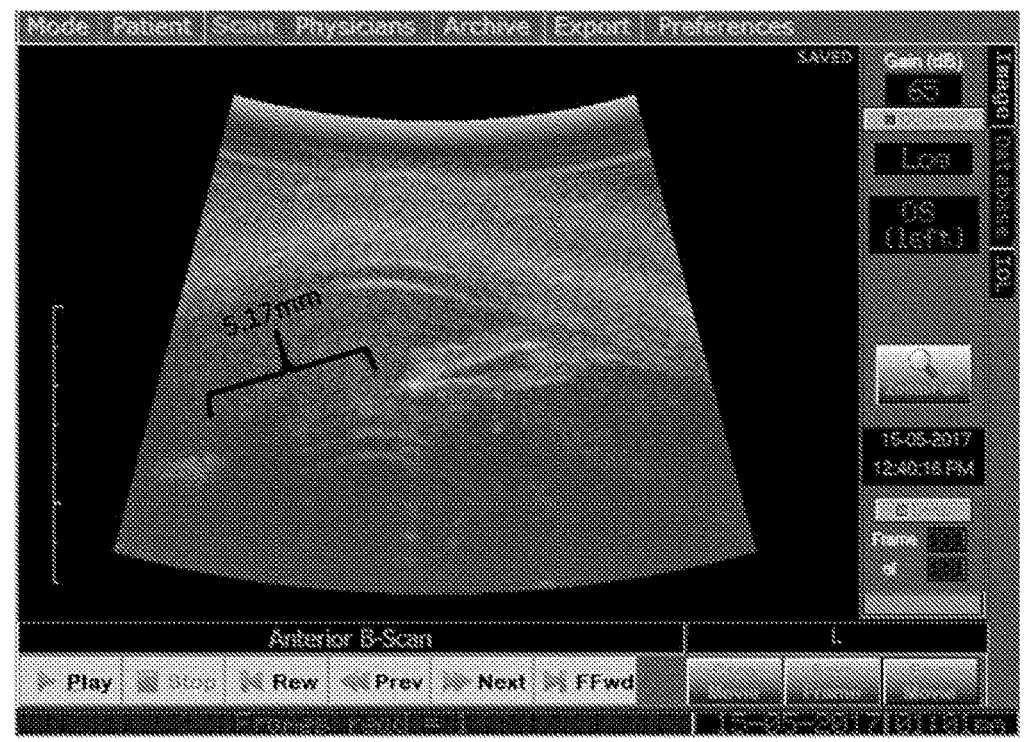
FIG. 14C shows a representative ultrasound image of a subject's eye, when looking sideways.

Ocular ultrasound was performed on a control subject's left eye in a dark room. A diameter of the subject's pupil was marked on the ultrasound output image and its size determined using ultrasound processing, as described herein. As seen in FIG. 14A the subject's pupil diameter was readily detectable and measured to be 5.15 mm. The procedure was repeated after inducing a pupillary reflex by transmitting visible light toward the subject's closed eye. In response to light, the subject's pupil decreased as expected (to 3.87 mm), as seen in FIG. 14B. The procedure was once again repeated while the subject was requested to look to the side. As seen from FIG. 14C, the determined pupil size (5.17 mm) was essentially identical to that determined when the subject was looking straight forward (FIG. 14A—5.15 mm).

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof. Unless otherwise defined, all technical and scientific terms used herein have the same meaning as commonly understood by one of ordinary skill in the art to which this invention belongs.

Unless specifically stated otherwise, as apparent from the following discussions, it is appreciated that throughout the specification discussions utilizing terms such as "processing", "computing", "calculating", "determining", "estimating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

The invention may be described in the general context of computer-executable instructions, such as program modules, being executed by a computer. Generally, program modules include routines, programs, objects, components, data structures, and so forth, which perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

According to some embodiments, the terms "approximately" and "about" may refer to +/−0.5%, +/−1%, +/−2%, +/−5%, or +/−10%. Each possibility is a separate embodiment.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A device for pupil size and/or pupillary reflex assessment in a subject having closed eyelids, the device comprising:
one or more light sources configured to transmit light toward a vitreous cavity of the subject; and
one or more detectors configured to detect a portion of the transmitted light exiting the subject's pupil through the closed eye;
wherein the one or more light source comprises a non-inductive light source and/or a reflex inductive light source,
wherein said non-inductive light source is configured to transmit light having a wavelength in a range of 750 nm-1000 nm and wherein said inductive light source is configured to transmit light having a wavelength in a range of 400 nm-700 nm.

2. The device of claim 1, wherein said one or more detectors is a digital camera, configured to image the subject's pupil through the subject's closed eye.

3. The device of claim 2, further comprising a processor configured to determine the subjects pupil size, based on an image analysis of at least one image obtained from the digital camera, wherein the image analysis comprises segmentation of the image to extract an area and/or contour and/or shape of the subject's pupil.

4. The device of claim 3, wherein the pupil size and/or the pupillary reflex is determined separately for each pupil and wherein said processor is further configured to compare the sizes of each of the subject's pupils and/or the pupillary reflex of each pupil.

5. The device of claim 3, wherein said processor is further configured to compare the determined pupil size and/or the pupillary reflex to a baseline pupil size and/or a baseline pupillary reflex or to the subject's previously determined pupil size and/or pupillary reflex.

6. The device of claim 3, wherein said processor is further configured to trigger an alarm if an abnormal pupil size and/or an abnormal pupillary reflex is detected.

7. The device of claim 3, wherein said processor is configured to determine the subject's pupil size and/or pupillary reflex periodically and/or continuously.

8. The device of claim 2, wherein said digital camera is a charge-coupled device (CCD) or a complementary metal oxide semiconductor (CMOS).

9. The device of claim 1, wherein the reflex inductive light source is configured to transmit light through the subject's eyelid to the subject's eyes, thereby inducing a pupillary reflex and wherein the processor is further configured to determine the subject's pupillary reflex functioning based on a comparison of the pupil size determined before and after inducing the pupillary reflex.

10. The device of claim 1, comprising a platform unit configured to be worn and/or positioned on the subject's head, such that at least part of said platform unit is positioned in front of the subject's eyes; wherein said one or more non-inductive light sources, said one or more inductive light sources and/or said one or more light detectors are attached to said platform unit.

11. The device of claim 10, wherein said one or more light sources comprise at least two light sources positioned on said platform unit in such manner that light emitted by the two light sources is transmitted through the subject's temples and/or through a side of the subject's eye, when said platform unit is worn and/or positioned on the subject's head and wherein said one or more light sources is positioned on said platform unit, such that light is transmitted through the back of the subject's head, when said platform unit is worn and/or positioned on the subject's head.

12. The device of claim 10, wherein said platform unit is sized and shaped to prevent penetration of ambient light.

13. A method for determining pupil size of a subject having closed eyelids, the method comprising;
transmitting light having a wavelength in a range of 750 nm-1000 nm toward a vitreous cavity of the subject using one or more light sources;
detecting, using one or more light detectors, a portion of the transmitted light exiting the subject's pupil through the subject's closed eye,
wherein the one or more light source comprises a non-inductive light source and/or a reflex inductive light source,
wherein said non-inductive light source is configured to transmit light having a wavelength in a range of 750 nm-1000 nm and wherein said inductive light source is configured to transmit light having a wavelength in a range of 400 nm-700 nm.

14. The method of claim 13, further comprising determining the subject's pupil size, based on image analysis of at least one image obtained from the one or more detector, wherein the one or more light source comprises a non-inductive light source and/or a reflex inductive light source.

15. The method of claim 14, further comprising transmitting inductive light through the subject's closed eyelid to the subject's eye, thereby inducing a pupillary reflex; transmitting non-inductive light toward the vitreous cavity of the subject; imaging the subject's eye in response to the inducing of the pupillary reflex; and determining the subject's pupil size and/or pupillary reflex based on a comparison of the pupil size determined before and after inducing the pupillary reflex.

16. The method of claim 13, further comprising comparing the determined pupil size and/or the pupillary reflex to a baseline pupil size and/or a baseline pupillary reflex or comparing the determined pupil size and/or the pupillary reflex to the subject's previously determined pupil size and/or pupillary reflex.

17. A platform unit configured to be worn and/or positioned on the subject's head, such that at least part of said platform unit is positioned in front of the subject's eyes; wherein said platform unit comprises one or more non-inductive light sources, one or more inductive light sources and/or one or more light detectors; wherein said platform unit is sized and shaped to prevent penetration of light;

wherein said non-inductive light source is configured to transmit light having a wavelength in a range of 750 nm-1000 nm and wherein said inductive light source is configured to transmit light having a wavelength in a range of 400 nm-700 nm.

18. The platform unit of claim 17, wherein said one or more light sources comprise at least two light sources positioned on said platform unit in such manner that light emitted by the two light sources is transmitted through the subject's temples and/or through a side of the subject's eye, when said platform unit is worn and/or positioned on the subject's head, and wherein said one or more light sources is positioned on said platform unit, such that light is transmitted through the templates of the subject's head, when said platform unit is worn and/or positioned on the subject's head.

* * * * *